US009045740B2

(12) United States Patent
Martin et al.

(10) Patent No.: US 9,045,740 B2
(45) Date of Patent: Jun. 2, 2015

(54) MODIFIED T7-RELATED RNA POLYMERASES AND METHODS OF USE THEREOF

(71) Applicant: University of Massachusetts, Boston, MA (US)

(72) Inventors: Craig T. Martin, Amherst, MA (US); Luis Ramirez-Tapia, Sunderland, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 13/775,929

(22) Filed: Feb. 25, 2013

(65) Prior Publication Data

US 2013/0224793 A1    Aug. 29, 2013

Related U.S. Application Data

(60) Provisional application No. 61/602,936, filed on Feb. 24, 2012.

(51) Int. Cl.
*C12N 9/12* (2006.01)
*C12P 19/34* (2006.01)
*C12P 21/02* (2006.01)

(52) U.S. Cl.
CPC .............. *C12N 9/127* (2013.01); *C12P 19/34* (2013.01); *C12P 21/02* (2013.01); *C12N 9/1247* (2013.01); *C12Y 207/07006* (2013.01)

(58) Field of Classification Search
None
See application file for complete search history.

(56) References Cited

U.S. PATENT DOCUMENTS

| | | | | |
|---|---|---|---|---|
| 5,385,834 A * | 1/1995 | Ikeda | | 435/194 |
| 6,365,350 B1 * | 4/2002 | Hayashizaki | | 435/6.11 |
| 6,524,828 B1 * | 2/2003 | Liao et al. | | 435/91.1 |
| 7,507,567 B2 * | 3/2009 | Sugiyama et al. | | 435/194 |
| 8,105,813 B2 * | 1/2012 | Diener et al. | | 435/194 |
| 2004/0091854 A1 * | 5/2004 | Guillerez et al. | | 435/5 |
| 2004/0259089 A1 * | 12/2004 | Watahiki et al. | | 435/6 |
| 2011/0136181 A1 * | 6/2011 | Oe et al. | | 435/91.3 |
| 2011/0256589 A1 * | 10/2011 | Sobek et al. | | 435/91.1 |
| 2012/0064577 A1 * | 3/2012 | Coleman | | 435/91.3 |

FOREIGN PATENT DOCUMENTS

WO    WO 2009126632 A1 * 10/2009

OTHER PUBLICATIONS

Guillerez et al., "A mutation in T7 RNA polymerase that facilitates promoter clearance", Proceedings of the National Academy of Sciences USA, vol. 102, No. 7, pp. 5958-5963, 2005.*
Vahia et al., "Direct tests of the energetic basis of abortive cycling in transcription", Biochemistry, vol. 50, pp. 7015-7022, 2011.*

(Continued)

*Primary Examiner* — Rebecca Prouty
*Assistant Examiner* — Richard Ekstrom
(74) *Attorney, Agent, or Firm* — Wolf, Greenfield & Sacks, P.C.

(57) ABSTRACT

The invention relates to modified T7-related RNA polymerases and methods of use thereof. In some embodiments, the invention relates to modified T7-related RNA polymerases that transcribe RNA with reduced abortive cycling and increased efficiency compared with native T7-related RNA polymerases.

29 Claims, 9 Drawing Sheets

(56) References Cited

OTHER PUBLICATIONS

GenBank Accession No. AEH41021.1; GI No. 335335277; Jun. 15, 2011.*

Blast Sequence Alignment of AEH41021.1 and SEQ ID No. 1.*

Patra et al., "Isolation and characterization of mutant bacteriophage T7 RNA polymerases", Journal of Molecular Biology, vol. 224, pp. 307-318, 1992.*

Gross et al., "Characterization of bacteriophage T7 RNA polymerase by linker insertion mutagenesis", Journal of Molecular Biology, vol. 228, pp. 488-505, 1992.*

Guo et al., "Protein tolerance to random amino acid change", Proceedings of the National Academy of Sciences USA, vol. 101, No. 25, pp. 9205-9210, 2004.*

Guillerez et al., A mutation in T7 RNA polymerase that facilitates promoter clearance. Proc Natl Acad Sci U S A. Apr. 26, 2005;102(17):5958-63. Epub Apr. 14, 2005.

McAllister et al., The phage RNA polymerases are related to DNA polymerases and reverse transcriptases. Mol Microbiol. Oct. 1993;10(1):1-6.

Theis et al., Topological and conformational analysis of the initiation and elongation complex of t7 RNA polymerase suggests a new twist. Biochemistry. Oct. 12, 2004;43(40):12709-15.

* cited by examiner

```
T7RP         LIE  STQMVSLHRQ  MAGVVGQD..  .SETTELAPE  YAEATATRAG  ALAGISMFQ  PCVVPPKPWT
T3RP         LIE  STGLVELQRH  NAGNAGSD..  .HEALQLAQE  YVDVLAKRAG  ALAGISMFQ  PCVVPPKPWV
K11          LIE  GTGLVEMTKN  KMADGSDDVT  SMQWVQLAPA  FVELLSKRAG  ALAGISPHQ  PCVVPPKPWV
BA14         LIG  STGLVELHRP  FAGNVEKD..  .GEYIQLTEQ  YVDLLSKRAG  ALAAIAPMYQ PCVVPPKPWT
Vibrio       LIE  ATQMVQLERK  FKGIPDKD..  .HEALHLAPE  YVEKLTNRAH  ALAGISPMYQ PMIVKPKPWT
Pseudomonas  LIE  SSGLVRITRR  SAGNVKED..  .CNVLELEPQ  WVEMLNQRAF  TLAGVNTYHQ PCVVPPRPWT
SP6          LEG  SVFYNGEPYF  MRAMRTYGGK  TIYYLQTSES  VGQWISAFKE  HVAQLSPAYA PCVIPPRPWR T7RP         AVYRKQKARK  SRRISLEFML  EQANKFANHK  AIWFPYNMDW  SEQ ID NO: 17
T3RP         ALKEWKKAAA  GIYRLDKARV  SRRISLEFML  EQANKFASKK  SEQ ID NO: 18
K11          ARKAWRKEAA  AVYRKDKARQ  SRRLSMEFMV  AQANKFANHK  SEQ ID NO: 19
BA14         ALKAWKKAAS  AIYRKEKARV  SRRMSMEFML  GQANKFAQFK  SEQ ID NO: 20
Vibrio       SLKKWKKAAA  AIYRKEKARQ  SRRISLEFAL  SQANKFSKYN  SEQ ID NO: 21
Pseudomonas  ARNAWKKQAS  GVYRSESSRV  SRRMSLETTL  ETARKFADFE  SEQ ID NO: 22
SP6          KEMLSPEQWQ  QFINWKGECA  RLYTAETKRG  SKSAAVVRMV  SEQ ID NO: 23
```

MODIFIED T7-RELATED RNA POLYMERASES AND METHODS OF USE THEREOF

RELATED APPLICATION

This application claims priority to U.S. Provisional Application No. 61/602,936, filed on Feb. 24, 2012, the content of which is hereby incorporated by references in its entirety.

FEDERALLY SPONSORED RESEARCH

This invention was made with government support under grant no. R01 GM055002 awarded by the National Institutes of Health. The government has certain rights in the invention.

FIELD OF THE INVENTION

The invention relates to RNA polymerases and methods of use thereof.

BACKGROUND OF INVENTION

Ribonucleic acids (RNA) are the subject of ongoing research in a basic science context as well as in a clinically-directed context where RNAs are used as therapeutic agents, drug targets, and informative biomarkers. New ventures have been formed around the use of RNAs as research tools, therapeutics, and/or diagnostics, and many existing companies have established RNA-related research and new product initiatives. In addition, there has been a significant increase in knowledge of previously uncharacterized noncoding RNAs over the past decade, and structure/function studies of such RNAs are ongoing. Such studies often involve the use of chemical RNA synthesis techniques to obtain RNAs under investigation. However, such techniques are often limited by low yields, including at lengths as short as 50 bases.

T7-related RNA polymerases, such as those from the bacteriophages T7, T3, SP6, or K11, and others are frequently used to synthesize RNA in vitro and in vivo. T7-related RNA polymerases may be used to obtain RNAs of any length in high yield and purity. Expression plasmids used in molecular biological research routinely include promoters for these polymerases (e.g., T7, T3, SP6 promoters) in their flanking sequences, and early references reporting protocols for large scale in vitro synthesis of RNA using such polymerases are widely cited.

SUMMARY OF INVENTION

While traditional T7-related RNA polymerases often transcribe sequences beyond the first ten or so bases of template nucleic acid with reasonably high fidelity, transcription of these bases is often performed with a significant degree sequence variability and often with short abortive products being produced (often with a molar ratio of abortive to desired full length of 100 or more). Aspects of the invention relate to the recognition that such abortive cycling can impose limitations on the initial sequence of the RNA and that this may be a particular problem for applications that involve synthesis of RNA probes and noncoding RNA molecules (e.g., miRNAs, siRNAs), among other RNAs. Accordingly, in some embodiments of the invention modified T7-related RNA polymerases are provided that are useful for synthesizing RNAs with reduced abortive cycling. In some embodiments, the modified T7-related RNA polymerases exhibit improvements in purity and/or yield of RNA synthesis products. Thus, in some embodiments, modified T7-related RNA polymerases are provided that offer improved tools to enable RNA research.

According to some aspects of the invention, a modified T7-related RNA polymerase is provided that has at least one amino acid insertion within its C-linker motif compared with a corresponding native form of the modified T7-related RNA polymerase. In certain embodiments, the insertion results in a reduced level of abortive product release compared with the corresponding native form of the T7-related RNA polymerase. In certain embodiments, the insertion results in a reduced energetic barrier to rotation of its N-terminal platform compared with the corresponding native form of the T7-related RNA polymerase. In certain embodiments, the insertion comprises a glycine, alanine, serine, threonine, cysteine, glutamine, asparagine, glutamate, aspartate, lysine, arginine or another amino acid. In certain embodiments, the insertion comprises up to 2, up to 3, up to 4, or up to 5 amino acids. In some embodiments, the amino acid sequence of the modified T7-related RNA polymerase has at least 85%, at least 90%, at least 95%, or at least 99% sequence homology compared with the corresponding native form of the T7-related RNA polymerase.

In some embodiments, a modified T7-related RNA polymerase has, in addition to an alteration (e.g., insertion) in its C-linker, at least one amino acid alteration compared with the corresponding native form of the modified T7-related RNA polymerase. In certain embodiments, the at least one additional amino acid alteration affects NTP selectivity of the polymerase. In some embodiments, other than the insertion in the C-linker motif, the amino acid sequence of the modified T7-related RNA polymerase is identical to the corresponding native form of the T7-related RNA polymerase.

In some embodiments the amino acid sequence of the corresponding native form of a modified T7-related RNA polymerase is set forth in any one of SEQ ID NOs: 1 to 4. In some embodiments in which the amino acid sequence of the corresponding native form of the modified T7-related RNA polymerase is set forth in SEQ ID NO: 1, the modified T7-related RNA polymerase comprises an amino acid insertion immediately before the amino acid at position 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, and/or 272. In certain to embodiments, this insertion is immediately before the amino acid at position 243, 247, 252, 259, 265 and/or 266. In one embodiments, this insertion is immediately before the amino acid at position 243, 252, and/or 259. In some embodiments, a modified T7-related RNA polymerase has the amino acid sequence of SEQ ID NO: 5 or 6.

In some embodiments, the C-linker motif of the corresponding native form of a modified T7-related RNA polymerase has a sequence as set forth in any one of SEQ ID NOs: 7 to 15. In certain embodiments, one or more of the amino acids of the C-linker motif are replaced with a conservative amino acid substitution. In certain embodiments, a modified T7-related RNA polymerase comprises an amino acid insertion immediately before the amino acid at position 1, 2, 3, 4, 5, 6, 7, 8, 9, 10, 11, 12, 13, 14, 15, 16, 17, 18, 19, 20, 21, 22, 23, 24, 25 26 27, 28, 29, 30, or 31 of its C-linker motif.

In some embodiments, an inserted amino acid is a glycine or alanine. However, in some embodiments, the inserted amino acid is alanine, arginine, asparagine, aspartate, cysteine, glutamine, glutamate, glycine, histidine, isoleucine, leucine, lysine, methionine, phenylalanine, proline, serine, threonine, tryptophan, tyrosine, or valine.

In some embodiments in which the amino acid sequence of the corresponding native form of the modified T7-related RNA polymerase is set forth in SEQ ID NO: 1, the modified T7-related RNA polymerase comprises a deletion of the amino acid at position 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, and/or 272.

According to some aspects of the invention, a modified T7-related RNA polymerase is provided that has at least one amino acid alteration that disrupts the alpha-helical structure of its C-linker motif such that abortive product release is reduced compared with the corresponding native form of the T7-related RNA polymerase. According to some aspects of the invention, a modified T7-related RNA polymerase is provided that has at least one amino acid alteration that disrupts at least one intramolecular contact between its C-linker motif and its O-helix motif such that abortive product release is reduced compared with the corresponding native form of the T7-related RNA polymerase. In some embodiments, if the corresponding native form of the modified T7-related RNA polymerase has a sequence as set forth in SEQ ID NO: 1, then the at least one amino acid alteration is not a substitution of the proline at position 266 with a leucine. In some embodiments, if the corresponding native form of the modified T7-related RNA polymerase has a sequence as set forth in SEQ ID NO: 2, then the at least one amino acid alteration is not a substitution of the proline at position 267 with a leucine. In some embodiments, if the corresponding native form of the modified T7-related RNA polymerase has a sequence as set forth in SEQ ID NO: 3, then the at least one amino acid alteration is not a substitution of the proline at position 239 with a leucine. In some embodiments, if the corresponding native form of the modified T7-related RNA polymerase has a sequence as set forth in SEQ ID NO: 4, then the at least one amino acid alteration is not a substitution of the proline at position 289 with a leucine. In some embodiments, if the sequence of the corresponding native form of the modified T7-related RNA polymerase is as set forth in SEQ ID NO: 1, then the alteration is an amino acid deletion of, or insertion at a position adjacent to, the amino acid at 245, 248, 249, 252, 259, 392, 389, 266, 267, 269, 400, or 407. In some embodiments, if the sequence of the corresponding native form of the modified T7-related RNA polymerase is as set forth in SEQ ID NO: 1, then the alteration is an amino acid substitution at 245, 248, 249, 252, 259, 392, 389, 266, 267, 269, 400, or 407.

In some embodiments, if the corresponding native form of the modified T7-related RNA polymerase has a sequence as set forth in SEQ ID NO: 1, then the at least one amino acid alteration is a substitution of the proline at position 266 with a cysteine. In some embodiments, if the corresponding native form of the modified T7-related RNA polymerase has a sequence as set forth in SEQ ID NO: 2, then the at least one amino acid alteration is a substitution of the proline at position 267 with a cysteine. In some embodiments, if the corresponding native form of the modified T7-related RNA polymerase has a sequence as set forth in SEQ ID NO: 3, then the at least one amino acid alteration is a substitution of the proline at position 239 with a cysteine.

In some embodiments, if the corresponding native form of the modified T7-related RNA polymerase has a sequence as set forth in SEQ ID NO: 1, then the at least one amino acid alteration is a substitution of the phenylalanine at position 266 with an alanine.

According to some aspects of the invention, nucleic acids are provided that comprise a sequence encoding a modified T7-related RNA polymerase. According to some aspects of the invention, expression vectors are provided that comprise the nucleic acid encoding a modified T7-related RNA polymerase operably linked to a promoter. According to some aspects of the invention, cells are provided that are engineered to express a modified T7-related RNA polymerase (e.g., cells that harbor a nucleic acid encoding a modified T7-related RNA to polymerase).

According to some aspects of the invention, methods are provided for producing an RNA. In some embodiments, the methods comprise combining a modified T7-related RNA polymerase with a nucleic acid template that encodes an RNA (e.g., mRNA, miRNA) and is operably linked with a promoter recognized by the modified T7-related RNA polymerase, under conditions suitable for RNA transcription, and maintaining the combination for a period of time sufficient to transcribe the RNA, thereby producing the RNA. According to some aspects of the invention, methods are provided for producing a protein. In some embodiments, the methods comprise (i.) combining a modified T7-related RNA polymerase with a nucleic acid template that encodes an mRNA and is operably linked with a promoter recognized by the modified T7-related RNA polymerase, under conditions suitable for RNA transcription, and maintaining the combination for a period of time sufficient to transcribe the mRNA; and (ii.) subjecting the transcribed mRNA to a translation reaction, thereby producing the protein. In some embodiments of the methods, compared with the corresponding native form of the T7-RNA polymerase, the modified T7-related RNA polymerase produces RNA with less release of abortive RNA fragments.

According to some aspects of the invention, kits are provided that comprise a container housing a modified T7-related RNA polymerase. In some embodiments, the kits further comprise a container housing a buffer (e.g., a reaction buffer or storage buffer). In some embodiments, the kits further comprise at least one container housing a research reagent (e.g., a reagent for preparing a labeled RNA probe or for performing an in vitro translation reaction).

BRIEF DESCRIPTION OF DRAWINGS

FIG. 5 depicts a sequence alignment SEQ ID NOs: 17-23 of T7-related RNA polymerases at the region of the C-linker and O helix;

DETAILED DESCRIPTION OF CERTAIN EMBODIMENTS OF THE INVENTION

Figure 1:
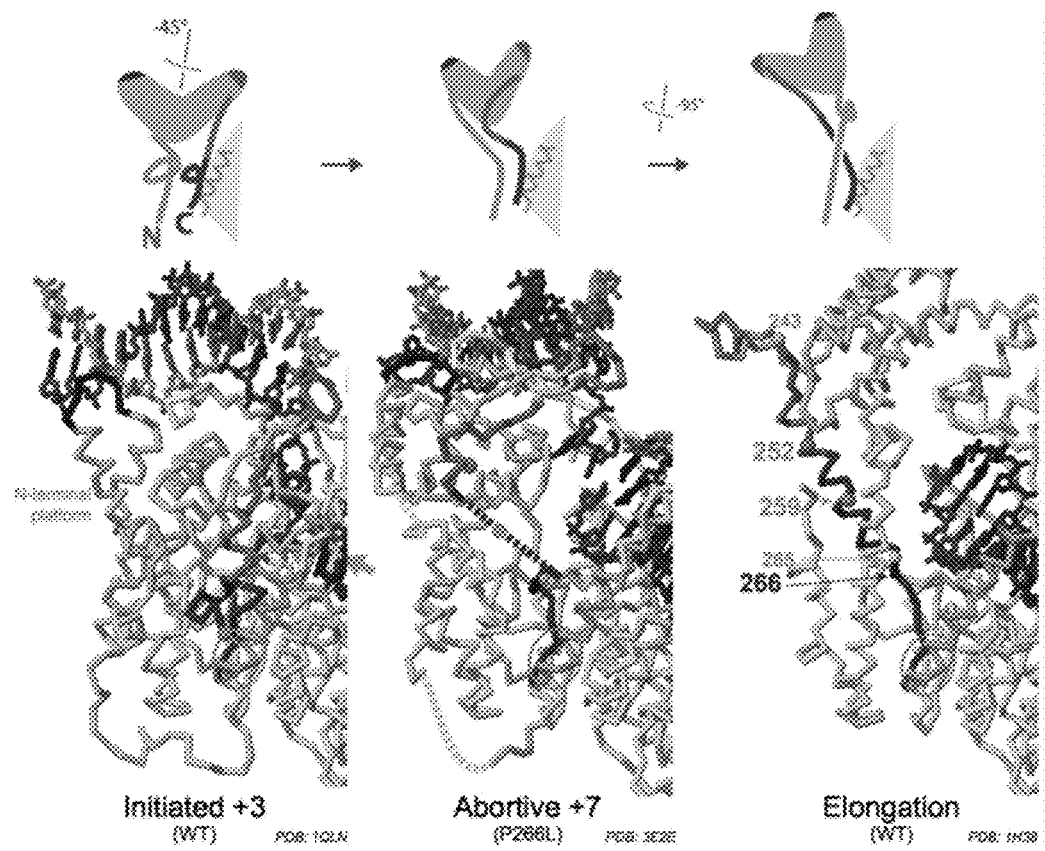
FIG. 1 provides a structural model for mutant T7-related RNA polymerase phenotypes.

Modified T7-related RNA polymerases are provided herein. These polymerases are useful for synthesizing RNAs in vitro and in vivo. In some embodiments, the modified T7-related RNA polymerases exhibit improvements in purity and/or yield of RNA synthesis products and reduce abortive cycling. As used herein the term, "T7-related RNA polymerase" refers to a RNA polymerase that is functionally and structurally related to an RNA polymerase of bacteriophage T7. The term T7-related RNA polymerases encompasses both single subunit polymerases (e.g., a T7, T3, K11, SP6 RNA polymerase) and multi-subunit polymerases (e.g., a two subunit RNA polymerase, e.g., a mitochondrial RNA polymerases, chloroplast RNA polymerase). Typically, T7-related RNA polymerases exhibit DNA-dependent RNA polymerase activity. T7-related RNA polymerases may specifically bind to and initiate transcription from a T7, T3, K11, SP6, or similar promoter binding site. T7-related RNA polymerases include members of the T7 family of RNA polymerases (See, e.g., McAllister W T, Raskin C A. *The phage RNA polymerases are related to DNA polymerases and reverse transcriptases Mol Microbiol.* 1993 October; 10(1):1-6.).

T7-related RNA polymerases may have at least 50%, at least 60%, at least 70%, at least 80%, at least 85%, at least 88%, at least 90%, at least 95%, or at least 99% sequence homology with a sequence as set forth in any of SEQ ID NOs: 1 to 4, which correspond to RNA polymerase sequences from bacteriophage T7, T3, SP6, K11, respectively. T7-related RNA polymerases include polymerases that, in their native form, have a sequence as set forth in any of SEQ ID NOs: 1 to 4.

T7-related RNA polymerases include polymerases that, in their native form, have a rotational N-terminal DNA binding platform linked to a C-terminal portion through an alpha-helical C-linker. T7-related RNA polymerases may have a C-linker that has at least 50%, at least 60%, at least 70%, at least 80%, at least 85%, at least 88%, at least 90%, at least 95%, or at least 99% sequence homology with a C-linker of a T7, T3, K11, or SP6 RNA polymerase. T7-related RNA polymerases may have a C-linker that has at least 50%, at least 60%, at least 70%, at least 80%, at least 85%, at least 88%, at least 90%, at least 95%, or at least 99% sequence homology with a sequence as set forth in any one of SEQ ID NOs: 7-14.

As used herein the term, "modified T7-related RNA polymerase" refers to a T7-related RNA polymerase having one or more amino acid sequence alterations (e.g., a substitution, deletion, insertion) compared with the corresponding native form of the polymerase. A modified T7-related RNA polymerase may have an alteration (e.g., an insertion in its C-linker) that results in a reduced level of abortive product release compared with the corresponding native form of the T7-related RNA polymerase. A modified T7-related RNA polymerase may have an alteration (e.g., an insertion in its C-linker) that results in a reduced energetic barrier to rotation of its N-terminal platform compared with the corresponding native form of the T7-related RNA polymerase.

A modified T7-related RNA polymerase may have at least one amino acid insertion within its C-linker motif compared with a corresponding native form of the recombinant T7-related RNA polymerase. For example, an insertion may be immediately before the amino acid at position 1, 2, 3, 4, 5, 6, 7, 8, 9, 10, 11, 12, 13, 14, 15, 16, 17, 18, 19, 20, 21, 22, 23, 24, 25 26 27, 28, 29, 30, or 31 of the C-linker motif.

A modified T7-related RNA polymerase may have an insertion in its C-linker that comprises any amino acid. In some embodiments, the modified T7-related RNA polymerase has an insertion in its C-linker that comprises one or more of a glycine, alanine, serine, threonine, cysteine, glutamine, asparagine, glutamate, aspartate, lysine or arginine. A modified T7-related RNA polymerase may have an insertion in its C-linker that comprises up to 2, up to 3, up to 4, up to 5, up to 6, up to 7, up to 8, up to 9, up to 10, or more amino acids. A modified T7-related RNA polymerase may have insertions at one or more positions in the C-linker. A modified T7-related RNA polymerase may have insertions at 1, 2, 3, 4, 5, or more positions.

It should be appreciated that amino acids in the C-linker motif may in some instances be replaced with conservative amino acid substitutions. For example, in instances where the C-linker motif of the corresponding native form of the T7-related RNA polymerase has a to sequence as set forth in any one of SEQ ID NOs: 7 to 15 and the modified form has one or more amino acid insertions in the C-linker motif, one or more of amino acids of the native form of the C-linker motif may be replaced with a conservative amino acid substitution.

The amino acid sequence of the modified T7-related RNA polymerase may have at least 85%, at least 90%, at least 95%, or at least 99% sequence homology compared with the corresponding native form of the T7-related RNA polymerase. A modified T7-related RNA polymerase may have at least 1, at least 2, at least 3, at least 4, or at least 5 additional amino acid alterations compared with the corresponding native form of the modified T7-related RNA polymerase. A modified T7-related RNA polymerase may have up to 1, up to 2, up to 3, up to 4, up to 5, or up to 10 amino acid alterations (e.g., in addition to an alteration in its C-linker motif) compared with the corresponding native form of the modified T7-related RNA polymerase. A modified T7-related RNA polymerase may comprise at least one amino acid alteration that affects NTP selectively, such that the modified T7-related RNA polymerase permits incorporation of modified nucleotides. However, in some embodiments, other than the insertion in the C-linker motif, the amino acid sequence of a modified T7-related RNA polymerase may be identical to the corresponding native form of the T7-related RNA polymerase.

The corresponding native form of a T7-related RNA polymerase may be the form of a single subunit RNA polymerase of bacteriophage T7, T3, SP6 or K11, or another native RNA polymerase. The corresponding native form of the T7-related RNA polymerase may have a sequence as set forth in SEQ ID NOs: 1 to 4, which correspond to RNA polymerase sequences from bacteriophage T7, T3, SP6, K11, respectively. When the amino acid sequence of the corresponding native form of the T7-related RNA polymerase is as set forth in SEQ ID NO: 1, the modified T7-related RNA polymerase may have an amino acid insertion immediately before one or more of the amino acids at positions 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, and 272. When the amino acid sequence of the corresponding native form of the T7-related RNA polymerase is as set forth in SEQ ID NO: 1, the modified T7-related RNA polymerase may have an amino acid insertion immediately before one or more of the amino acids at positions 243, 247, 252, 259, 265 and/or 266. When the amino acid sequence of the corresponding native form of the T7-related RNA polymerase is as set forth in SEQ ID NO: 1, the modified T7-related RNA polymerase may have an amino acid insertion immediately before one or more of the amino acids at positions 243, 252, and/or 259. For example, the modified T7-related RNA polymerase may have the amino acid sequence of SEQ ID NO: 5 or 6. A modified T7-related RNA polymerase may have any insertion indicated in Table 1.

Certain Alterations Relating to the C-linker of T7-related RNA Polymerases

In some embodiments, a modified T7-related RNA polymerase has at least one amino acid alteration that disrupts the alpha-helical structure of its C-linker motif such that abortive product release is reduced compared with the corresponding native form of the T7-related RNA polymerase. In some embodiments, the modified T7-related RNA polymerase has at least one amino acid alteration that disrupts at least one intramolecular contact between its C-linker motif and its O-helix motif such that abortive product release is reduced compared with the corresponding native form of the T7-related RNA polymerase. For example, in instances where the sequence of the corresponding native form of the modified T7-related RNA polymerase is as set forth in SEQ ID NO: 1 (which corresponds to a RNA polymerase of bacteriophage T7), an alteration at position 245, 392, 389, 269 and/or 407, involving a deletion of the amino acid, insertion adjacent to the amino acid, or substitution of the amino acid, may disrupt one or more intramolecular contacts between the C-linker and O-helix such that abortive product release is reduced.

In some embodiments, if the corresponding native form of the modified T7-related RNA polymerase has a sequence as set forth in SEQ ID NO: 1, then the at least one amino acid alteration is not a substitution of the proline at position 266 with a leucine. In some embodiments, if the corresponding native form of the modified T7-related RNA polymerase has a sequence as set forth in SEQ ID NO: 2, then the at least one amino acid alteration is not a substitution of the proline at position 267 with a leucine. In some embodiments, if the corresponding native form of the modified T7-related RNA polymerase has a sequence as set forth in SEQ ID NO: 3, then the at least one amino acid alteration is not a substitution of the proline at position 239 with a leucine. And, in some embodiments, if the corresponding native form of the modified T7-related RNA polymerase has a sequence as set forth in SEQ ID NO: 4, then the at least one amino acid alteration is not a substitution of the proline at position 289 with a leucine.

Cells Engineered to Express Modified T7-related RNA Polymerase

In some embodiments, a modified T7-related RNA polymerase is produced using to recombinant DNA techniques. Thus, modified T7-related RNA polymerases may be produced in cells that have been engineered to express a modified form of a native T7-related RNA polymerase.

Cells that are engineered to express a T7-related RNA polymerase may comprise an exogenous nucleic acid encoding a modified T7-related RNA polymerase. The skilled artisan will appreciate that the exogenous nucleic acid may be delivered to the cells using methods well known in the art. For example, the exogenous nucleic acid may be transfected into the cells using lipid-based transfection reagents, virus-mediated gene transfer, calcium phosphate mediated transfection, or other technique. Standard cell biological methods may be used for selecting cells that have been transfected (e.g., cells that have incorporated the transgene into their genome or that harbor an episomal transgene). Appropriate selection genes (e.g., neomycin resistance gene, hygromycin resistance gene, blastocidin resistance gene, etc.) may be incorporated into the nucleic acid encoding modified T7-related RNA polymerase or provided in a separate nucleic acid delivered to the cells in parallel with the nucleic acid encoding modified T7-related RNA polymerase. Accordingly cells that have been stably transfected with an modified T7-related RNA polymerase encoding nucleic acid may be obtained using one or more selection drugs (e.g., neomycin, hygormycin, blastocidin, etc.) to eradicate cells that have not been stably transfected. Alternatively, cells that have been stably transfected with an modified T7-related RNA polymerase encoding nucleic acid may be obtained by a limited dilution cloning scheme.

Expression Vectors Encoding Modified T7-related Polymerases

The invention in some aspects provides nucleic acids (e.g., transgenes, expression vectors) that encode modified T7-related RNA polymerases. The nucleic acids may encode a T7-related RNA polymerase having at least 80%, 85%, 90%, 95%, 98%, or 99% homology with a sequence as set forth in any one of SEQ ID NOs: 1-4. It should be appreciated that nucleic acids encoding modified T7-related RNA polymerases may comprise regulatory sequences, gene control sequences, promoters, non-coding sequences and/or other appropriate sequences for expressing the modified T7-related RNA polymerases. Typically, the coding region is operably linked with one or more of these nucleic acid components.

Nucleic acids encoding a T7-related RNA polymerase may be incorporated in vector. As used herein, the term "vector" includes any genetic element, such as a DNA plasmid, which is capable of replication when associated with the proper control elements or replication conditions, and/or which can transfer gene sequences between cells. In some embodiments, useful vectors are contemplated to be those vectors in which the nucleic acid segment to be transcribed is positioned under the transcriptional control of a promoter. The term "expression vector" means any type of genetic construct containing a nucleic acid in which part or all of the nucleic acid encoding sequence is capable of being transcribed.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Gene control sequence" refers to the DNA sequences required to initiate gene transcription plus those required to regulate the rate at which initiation occurs. Thus a gene control sequence may consist of the promoter, where the general transcription factors and the polymerase assemble, plus all the regulatory sequences to which gene regulatory proteins bind to control the rate of these assembly processes at the promoter. For example, control sequences that are suitable for prokaryotes may include a promoter, optionally an operator sequence, and a ribosome-binding site. Eukaryotic cells may utilize promoters, enhancers, and/or polyadenylation signals.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions.

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid to tracts to the 3' end of the mRNA precursor.

The "translation leader sequence" or "5' non-coding sequences" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency.

The term "operatively linked" refers to the association of two or more nucleic acid fragments on a single nucleic acid fragment so that the function of one is affected by the other. For example, a promoter is operatively linked with a coding sequence when it is capable of affecting the expression of that coding sequence (i.e., that the coding sequence is under the transcriptional control of the promoter). Coding sequences can be operatively linked to regulatory sequences in sense or antisense orientation.

The coding region of a nucleic acid may include one or more silent mutations to optimize codon usage for a particular cell type. For example, the codons of the nucleic acid may be optimized for expression in a vertebrate cell. The codons of the nucleic acid may be optimized for expression in a mammalian cell. The codons of the nucleic acid may be optimized for expression in a human cell. The codons of the nucleic acid may be optimized for expression in a bacterium, bacteriophage or other expression system.

The nucleic acid may encode a modified T7-related polymerase that has one or more conservative amino acid substitutions, e.g., one or more conservative amino acid substitutions compared with any one of SEQ ID NO: 1-4. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art. Conservative substitutions of amino acids include substitutions made among amino acids within the following groups: (a) M, I, L, V; (b) F, Y, W; (c) K, R, H; (d) A, G; (e) S, T; (f) Q, N; and (g) E, D. Accordingly, conservative amino acid substitutions may provide functionally equivalent variants, or homologs of a protein.

Purification of Modified T7-related RNA Polymerases

Isolated cells of the invention may be used for the production of modified T7-related RNA polymerases. The isolated cells may be grown in a suitable culture medium and the modified T7-related RNA polymerases may be isolated from the cells and/or from the medium in which the cells are grown. Modified T7-related RNA polymerases may be obtained using purification methods known in the art, e.g., conventional chromatographic methods including immunoaffinity chromatography, hydrophobic interaction chromatography, size exclusion filtration, cation or anion exchange chromatography, high pressure liquid chromatography (HPLC), reverse phase HPLC, and similar methods. It is contemplated that methods of purification may, in some cases, include methods whereby the modified T7-related RNA polymerases is expressed and purified as a fusion protein having a specific tag, label, or chelating moiety that is recognized by a specific binding partner or agent. The purified protein can be cleaved to yield the desired protein, or can be left as an intact fusion protein. Cleavage of the fusion component may produce a form of the desired protein having additional amino acid residues as a result of the cleavage process.

Use of Modified T7-related RNA Polymerases

Modified T7-related RNA polymerases may be used for the synthesis of various forms of RNA. Examples of such forms of RNA include, but are not limited to, hybridization probes, RNase protection assay probes, templates for in vitro translation, precursor mRNAs for splicing or other processing studies, antisense RNAs, shRNAs, miRNAs, ribozymes, and dsRNAs for RNA interference, or gene silencing studies. T7-related RNA polymerases may be used to transcribe DNA that has been cloned into vectors that have appropriate promoters that are recognized by T7-related RNA polymerases. In some configurations, multiple promoters (e.g., T7 and T3, T7 and SP6, T3 and SP6, etc.) may be included in opposite orientations to enable synthesis of sense and antisense transcripts from the same template. Thus, in some configurations, RNA can be selectively synthesized from either strand of a template DNA using different polymerases. RNAs synthesized by T7-related RNA polymerases may be labeled (e.g., radioactively labeled, fluorescently labeled, biotin labeled, etc.) or non-labeled.

Methods for producing RNAs using T7-related RNA polymerases typically involve combining any of the modified T7-related RNA polymerases disclosed herein with a nucleic acid template that encodes an RNA and is operably linked with a promoter recognized by the modified T7-related RNA polymerase, under conditions suitable for RNA transcription, and maintaining the combination under these conditions for a period of time sufficient to transcribe the RNA, thereby producing the RNA. In applications where the transcript RNA is an mRNA for an in vitro translation assay to produce a protein of interest a further step of to subjecting the transcribed mRNA to a translation reaction (e.g., using a rabbit reticulocyte lysate translation system) may be used to produce the protein.

Kits and Related Compositions

Modified T7-related RNA polymerases described herein may, in some embodiments, be assembled into kits to facilitate their use, e.g., research applications. A kit may include one or more containers housing the modified T7-related RNA polymerases. The kits may also include one or more containers housing related reagents to be used with the T7-related RNA polymerases (e.g., buffers, labeling reagents, ribonucleotides, salts, etc.). The kit may include a container housing a reaction buffer and/or a container housing a storage buffer.

In some kits, the reaction buffer may include a mixture comprising one or more of the following: a buffering agent (e.g., Tris-HCL), salts (e.g., $MgCl_2$, NaCl), a reducing agent (e.g., Dithiothreitol), and an stimulating agent (e.g., BSA, spermidine)). In some kits, the storage buffer may include a mixture comprising one or more of the following: a buffering agent (e.g., Tris-HCL), a surfactant (e.g., a nonionic surfactant, such as Triton X-100), a reducing agent (e.g., 2-Mercaptoethanol), a chelating agent (e.g., EDTA), salts (e.g., NaCl), and a stabilizing agent (e.g., glycerol)). Kits for research purposes may contain the components in appropriate concentrations or quantities for running various experiments.

The kit may be designed to facilitate use of the methods described herein by researchers and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or reaction buffer), which may or may not be provided with the kit. In some kits the modified T7-related RNA polymerase may be provided in a storage buffer. In some kits, the modified T7-related RNA polymerase may be provided as a dry power or in a lyophilized form and the user may be provided with instruction for reconstituting the polymerase in a buffer (e.g., in a storage buffer).

The kit may also include instructions for use. As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual, internet, and/or web-based communications, etc.

EXAMPLES

Example 1

Mechanism-Based Protein Redesign—Modified T7-Related RNA Polymerases with Reduced Abortive Cycling Without wishing to be bound by theory, Applicants have developed a model for instability in initially transcribing complexes of T7-related RNA polymerases. During initial transcription (the abortive phase), growth of the RNA-DNA hybrid from 3 base pairs to at least 8 base pairs drives a rotation of an N-terminal platform protein domain. During this rotation, the N-terminal platform maintains contact with the double stranded promoter DNA. Applicants believe that this rotation ultimately (beyond 8 bases) leads to disruption of a substructure within the N-terminal platform and a disruption of DNA binding contacts. Loss of promoter contacts (once the hybrid is sufficiently long) are believed to be necessary to effect the transition to stable elongation, and a sequence-nonspecific elongation complex.

In developing this model, Applicants examined a structural model for mutant T7-related RNA polymerase phenotypes. Applicants determined that during initial transcription, a linker within a T7-related RNA polymerase (FIG. 1, residues 243 to 253, light brown; 254 to 272, brown) extends to accommodate rotation of the N-terminal platform (pink), which is driven by hybrid growth in the direction of the purple arrow. During this activity, contacts (light blue ovals) with the "O" helix (light green) are partially lost, allowing extension of the linker. Stress resulting from this extension drive a reversal of the motion, shortening the hybrid, decreasing its stability, and leading to abortive dissociation of the RNA.

Based in part on these structural observations, various modified T7-related RNA polymerases were produced having amino acid alterations within the region of the linker. Examples of these alterations include insertions of single Gly residues at positions 243, 252, 259, and 265. These alterations were identified as leading to more facile extension, lower energetic stress, and less abortive dissociation during initial transcription. Mutations of residues in the "O" helix that initially make and then lose contacts with the linker (interactions shown in the upper light blue circle in the "Initiated +3" structure of FIG. 1) were also identified as being capable of reducing energetic stress and thus leading to reduced abortive dissociation during initial transcription. In FIG. 1, dashed lines represent regions of unresolved electron density in the structures.

It was found that the modified T7-related RNA polymerases produced less abortive to RNA products. This finding is exemplified in FIG. 2, which shows results of 30 min transcription reactions performed at room temperature, with 0.5 µM polymerase, 0.25 µM DNA, 800 µM each NTP, 50 mM potassium glutamate, 30 mM Tris-Acetate, 15 mM magnesium acetate, 0.05% Tween 20, pH 7.8. Denaturing gel electrophoresis was performed in 10 mM Tris/Borate, 7 M urea, 20% acrylamide.

Figure 2:
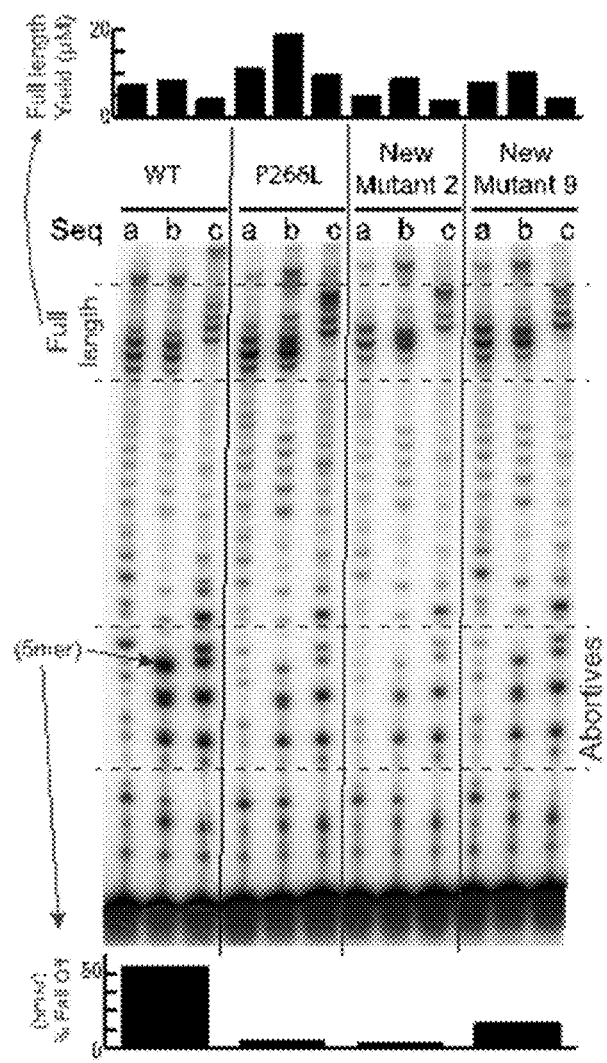
FIG. 2 depicts experimental results showing exemplary mutant T7-related RNA polymerases that produce less abortive products.
Figure 3:
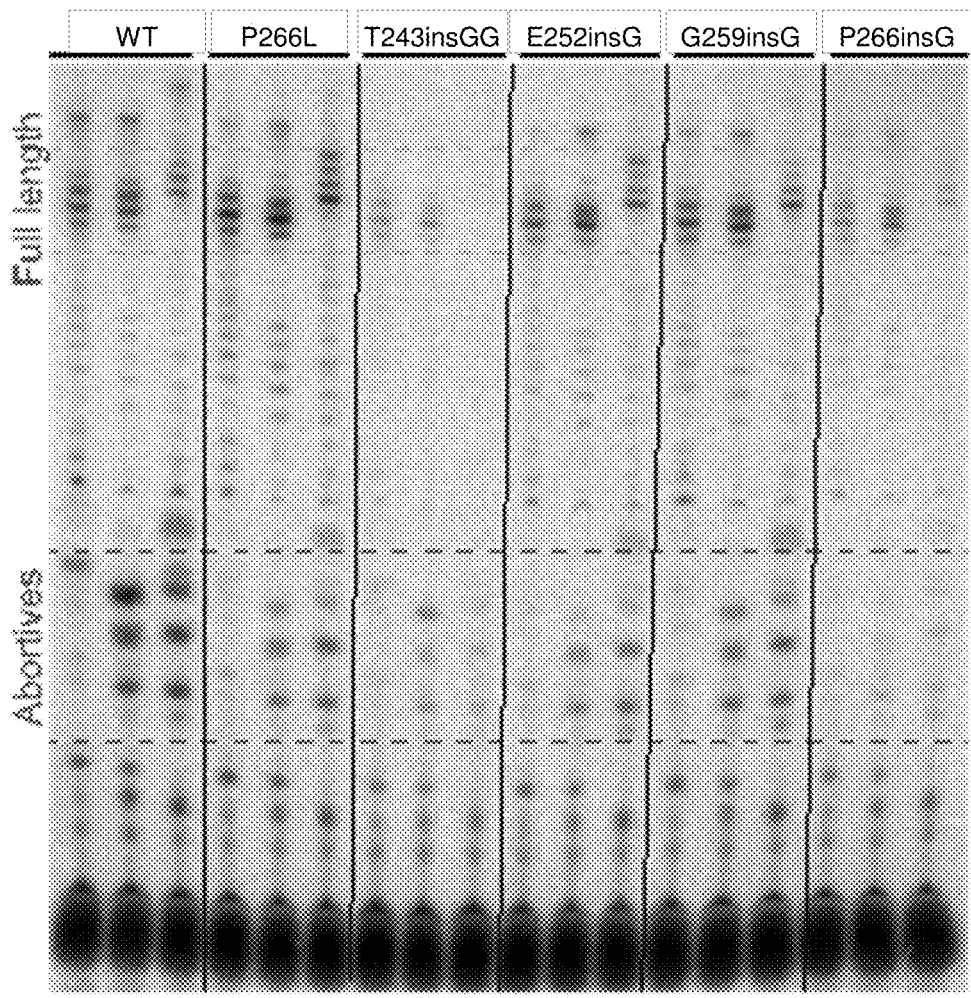
FIG. 3 depicts experimental results showing exemplary mutant T7-related RNA polymerases that produce less abortive products compared with P266L and wild-type T7 RNA polymerases.

The use of these modified forms of T7 RNA polymerase for RNA synthesis dramatically reduces the yield of undesired (short, abortive) transcripts in transcription. As shown in FIGS. 2 and 3 and summarized in Table 1, abortive impurities are dramatically reduced in these polymerases.

The results shown in FIG. 2 present transcription on three different DNA sequences (a, b, c), with (a) being a sequence that yields relatively few abortives, while (b) and (c) are sequences that produce primarily abortive products with the wild type enzyme. As for the currently commercialized mutant P266L, the two new mutations show dramatically reduced abortive fall off. For illustration, the lower bar chart quantifies the fraction of complexes that dissociate abortively at an RNA length of 5 bases on construct (b).

Mutant 2 represents the insertion of a single glycine residue prior to position 252 of T7 RNA polymerase, while mutant 9 represents the insertion of a single glycine residue prior to position 259. These residues lie in a linkage that becomes extended during initial transcription. Glycine insertions prior to positions 243 and 266 (not shown) also result in lower percentage amounts of abortives (but with lower overall transcription under certain conditions). These results support a model whereby any lengthening of this C-linker segment will yield the reduced abortive phenotypes.

TABLE 1

Summary of Modified T7-Related RNA Polymerases

| Mutation | Expression | Solubility | Phenotype |
|---|---|---|---|
| E252insG | Good | Good | Low abortive products compared to total run off; transcription phenotype is similar to P266L under certain conditions. |
| G259insG | Good | Relatively Fair | Low abortive products compared to total run off. This mutant shows a tendency to aggregate in transcription buffers compared with WT under certain conditions. |
| P266insG | Good | Good | Low abortive products compared to total run off, Overall transcription is decreased under certain conditions. |
| A247insG | Good | Relatively Poor | Expression levels are good. Protein may be insoluble for purification under certain conditions. |

TABLE 1-continued

Summary of Modified T7-Related RNA Polymerases

| Mutation | Expression | Solubility | Phenotype |
|---|---|---|---|
| T243insGG | Good | Good | Transcription initiation good. Transition to elongation may be affected under certain conditions. Approximately one turnover is observed under certain conditions. |

Mutant A262insG, was produced but sequence analysis showed a G insertion at position 247 affect solubility of the protein under certain conditions. This mutant was expressed as a double mutant A262insG/A247insG.

Different C-Linker Insertions Yield Similar Reduced Abortive Phenotype.

Applicants have targeted various mutations in the C-linker regions, as shown in the Table 1 and in FIG. 3. While E252insG and G259insG are the most active overall of those observed, other insertions in this region also yield a "reduced abortive" phenotype. This further supports a mechanistic model, in which lengthening of the C-linker in general reduces to strain in initially transcribing complexes, leading to reduced abortive cycling. Thus, other insertions in this region are generally expected to have the same overall property of reduced abortive dissociation.

Applicants have engineered different single amino acid deletions in this region. The model indicates that the resulting shortened linker will lead to higher strain and affect (e.g., increase) abortive propensity. Mutations include: Δ259/P266L, Δ252/P266L, Δ259/WT of the bacteriophage T7 RNA polymerase.

FIG. 3 shows the results of 5 min transcription reactions conducted at room temperature, with 0.5 μM polymerase, 0.5 μM DNA, 800 μM each NTP, 50 mM potassium glutamate, 30 mM Tris-Acetate, 15 mM magnesium acetate, 0.05% Tween 20, pH 7.8. Denaturing gel electrophoresis was performed in 10 mM Tris/Borate, 7 M urea, 20% acrylamide.

Comparison of the results depicted in FIGS. 2 and 3 indicate that the observed phenotype is not specific to reaction conditions. The data presented in FIG. 2 show the results of extended time (30 min) reactions, in contrast to those of FIG. 3 that show limited time (5 min) reactions. The results are essentially identical and indicate that the latter results are not perturbed depletion of NTP pools.

Example 2

T7-Related RNA Polymerase Phylogenetic Relationships

Figure 4:
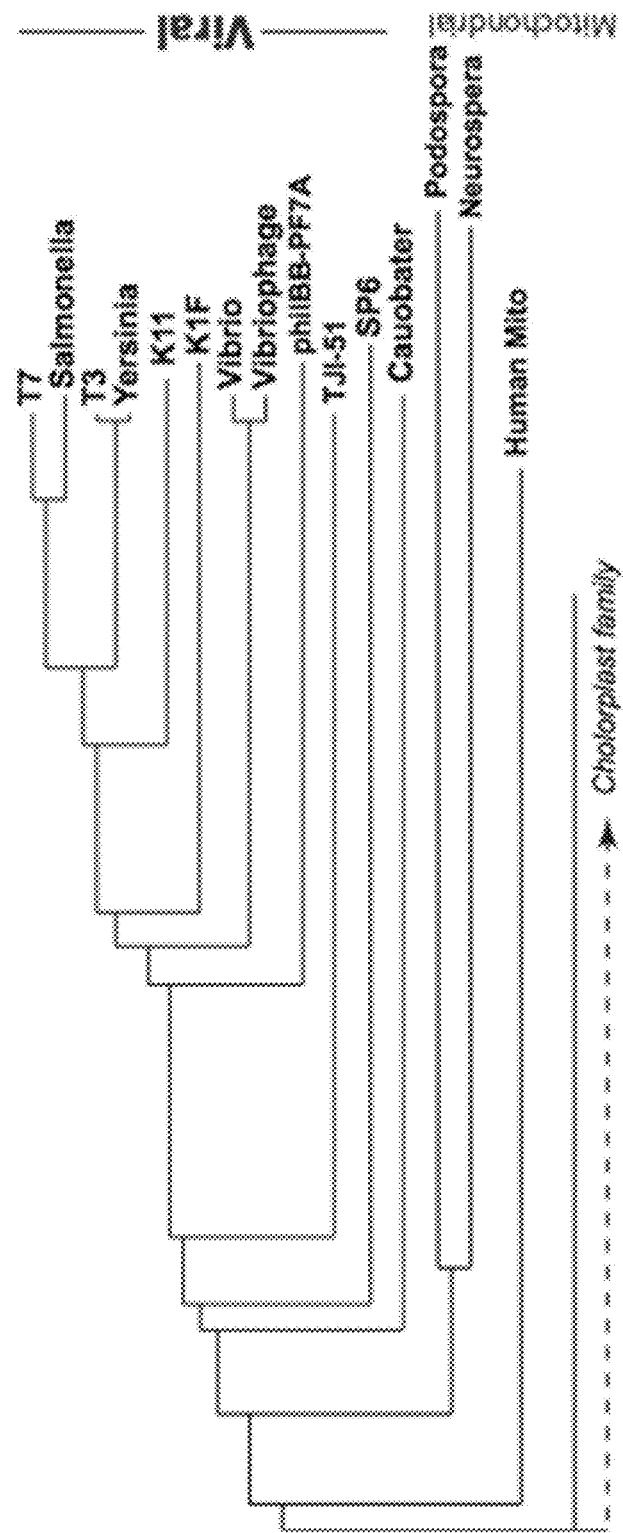
FIG. 4 depicts protein sequence phylogenetic relationships among T7-related RNA polymerases.

Applicants prepared an RNA polymerase protein sequence-derived phylogenetic tree shown in FIG. 4, which demonstrates that T7 RNA polymerase is closely related to the T3 and K11 RNA polymerases, as well as SP6 RNA polymerase and various mitochondrial and chloroplast RNA polymerases. Changes to the C-terminal linker are expected to have similar effects in the related viral RNA polymerases, e.g., T3, K11, SP6 RNA polymerases. Although single subunit RNA polymerases are less structurally related to certain multi-subunit bacterial and eukaryotic RNA polymerases, hybrid growth in these systems also is expected to produced a structural rearrangement in the protein that leads to promoter release.

FIG. 5 depicts a sequence alignment of T7-related RNA Polymerases around the region of the C-linker (upper) and in the O helix (lower). Lack of strict conservation supports the "linkage" role for this region and that a variety of different amino acids may be used to expand the linkage and affect abortive cycling, particularly in the region near mutation 251. Color coding in FIG. 5 corresponds to that of the structural figures. Sequence alignments within the C-terminal catalytic domain (residues 350-883) revealed significant active site conservation within these RNA polymerases. The N-terminal domain (1-350), which includes the N-terminal promoter binding platform, the refolding loop, and the C-linker is not directly involved in catalysis, but serves a relatively important structural role. Thus, in this context, structural conservation may be relatively more important than sequence conservation. For example, human mitochondrial RNA polymerase shows relatively low sequence conservation with the viral polymerases, yet crystal structures (3SPA, in FIG. 7) reveal that the overall structure of the N-terminal (and the C-terminal) domain is conserved.

Structural analysis indicates that insertions in the C-terminal leg region (242-268) are expected to yield phenotypes similar to the mutations noted above. FIG. 3 presents data from mutants containing insertions of a Gly before residue 266 and two Gly residues before residue 243. The abortive products are reduced relative to the full length.

Figure 6:
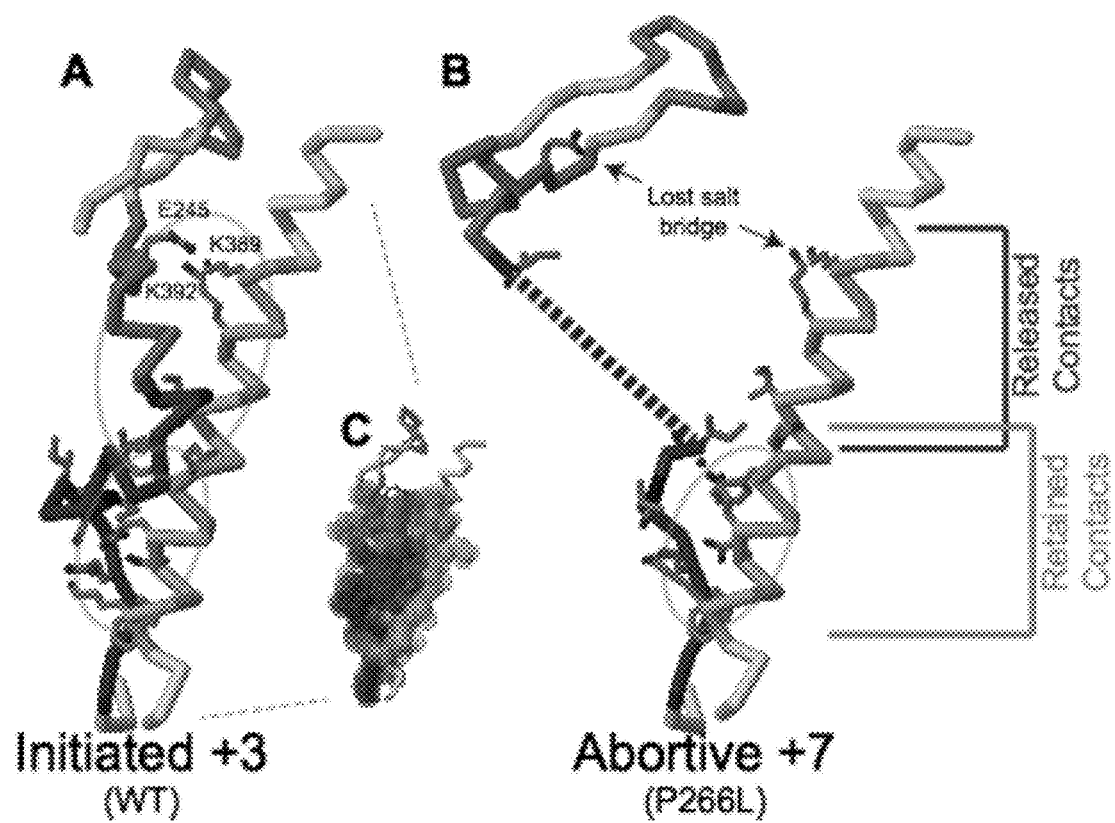
FIG. 6 depicts extension and contacts of a T7-related RNA polymerase.

Results of Applicants' structural analysis indicate that at least two classes of mutations lead to reduced abortive cycling. As depicted in FIG. 6, these mutations are classified by the nature of contacts between the C-linker and the O-helix. The contacts denoted as "Retained" in the figure persist through initiation, initial (abortive) transcription, and elongation. The second set of interactions is present in the "Initiated +3" structure, but are lost in the structure at +7. Insertion mutations that lengthen the C-linker (242 to 272) reduce the energetic barrier to rotation of the N-terminal platform and therefore the reciprocal stress that leads to abortive to product release. Since this region is alpha-helical, mutations that disrupt the helical structure of the linker will also facilitate extension. In addition, mutations that disrupt contacts between the C-linker (residues 242 to 272) and the "O" helix (residues 388 to 407) present a lower barrier to extension of the C-linker. FIG. 6 details contacts between these two regions, including salt bridges: Glu245, Lys392, Lys389 (labeled in the figure) and Gln269, Lys407 (within the lower interface), and including hydrophobic contacts across the interface.

Example 3

Analysis of Human Mitochondrial RNA Polymerase (hmtRP)

A comparison of the structure of human mitochondrial RNA polymerase with structures of T7 RNA polymerase at positions +3 and +7 was performed. The large C-terminal domain (grey domain to the right in each) aligned very well in all three cases, while the human mt RNA polymerase in the absence of DNA shows the N-terminal rotation characteristic of the T7 structure stepped out to approximately position +7.

Figure 8:
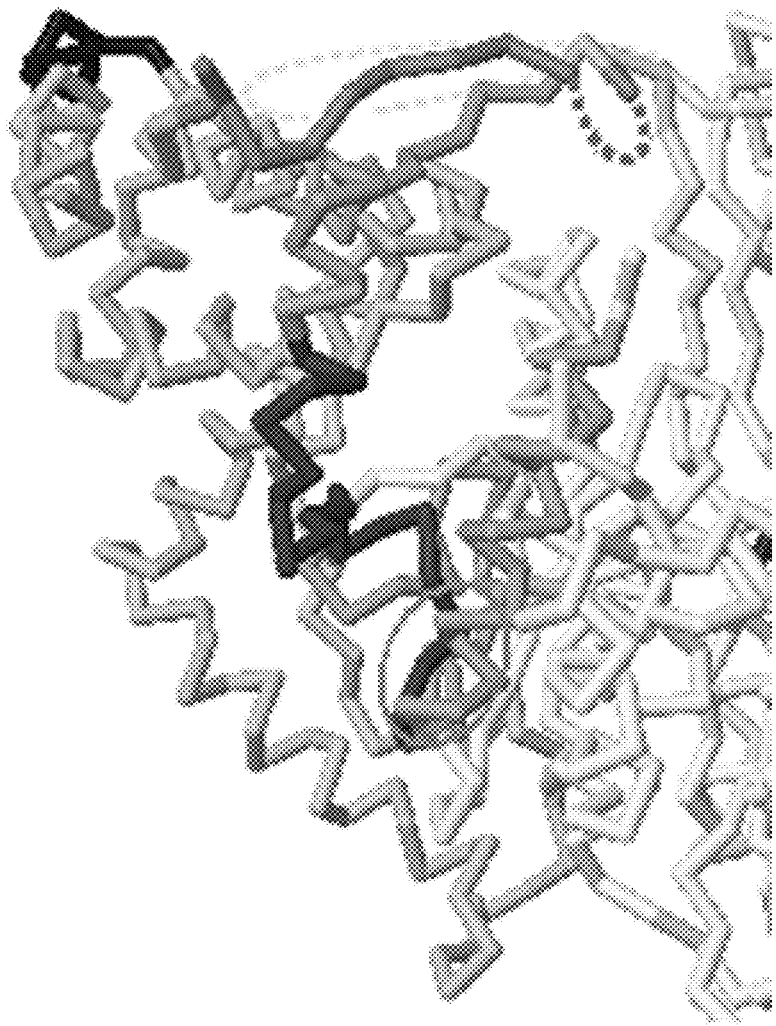
FIG. 8 depicts the structure of human mitochondrial RNA polymerase.

Note that the human mt RNA polymerase utilizes a secondary subunit for initiation, but not elongation. It also has an N-terminal addition (thin gray trace). FIG. 8 depicts the DNA-free structure of hmtRP. Color coding in FIG. 8 is the same as that used above for T7 RNA polymerase and is based on the sequence alignment presented in FIG. 5.

Figure 7:
FIG. 7 depicts a comparison of the structure of human mitochondrial RNA polymerase with structures of T7 RNA polymerase.

The crystal structure of the two-subunit RNA polymerase (hmtRP) from human mitochondria supports the structural understanding of the T7 family phage RNA polymerases. While this protein shares relatively low sequence homology with T7 RNA polymerase, there is relatively substantial structural homology. FIG. 7 compares the structure of the large subunit of human mitochondrial RNA polymerase, free of DNA, with the structures of the initiation (+3, WT) and initially transcribing (+7, P266L) T7 RNA polymerase structures. The large subunit of hmtRP (homologous to the T7 family RNA polymerases) utilizes a second subunit for promoter-specific initiation. Note that in the absence of the latter subunit, the N-terminal platform is rotated, as shown in FIG. 8, such that the complex should be (and is experimentally) relatively incompetent for initiation. Binding of the secondary subunit drives rotation back towards the T7 initiation structure at +3. As the enzyme transcribes up through position +7 to +10, rotation drives release of the smaller subunit, to allow the extension of the C-terminal leg, as above. Thus interactions with the initiation subunit at least influence interactions between the lower C-linker (brown) and the O helix (tan) in stabilizing the initiation configuration.

Human mitochondrial RNA polymerase shows sequence homology in key active site residues with RNA polymerases of bacteriophage T7, the structures are remarkably similar and the analysis indicate a similar mechanistic model in which hybrid growth both drives promoter release, and is "pushed back" by the N-terminal rotating platform. Thus in the C-linker, sequence is indicated as being relatively less important than connectivity and length of the linker. The mechanistic features that give rise to abortive cycling are the same, and indicate that analogous insertion mutations in other RNA polymerases (e.g., T3, K11, and SP6) will have the same properties of reduced abortive cycling.

Example 4

Figure 9:
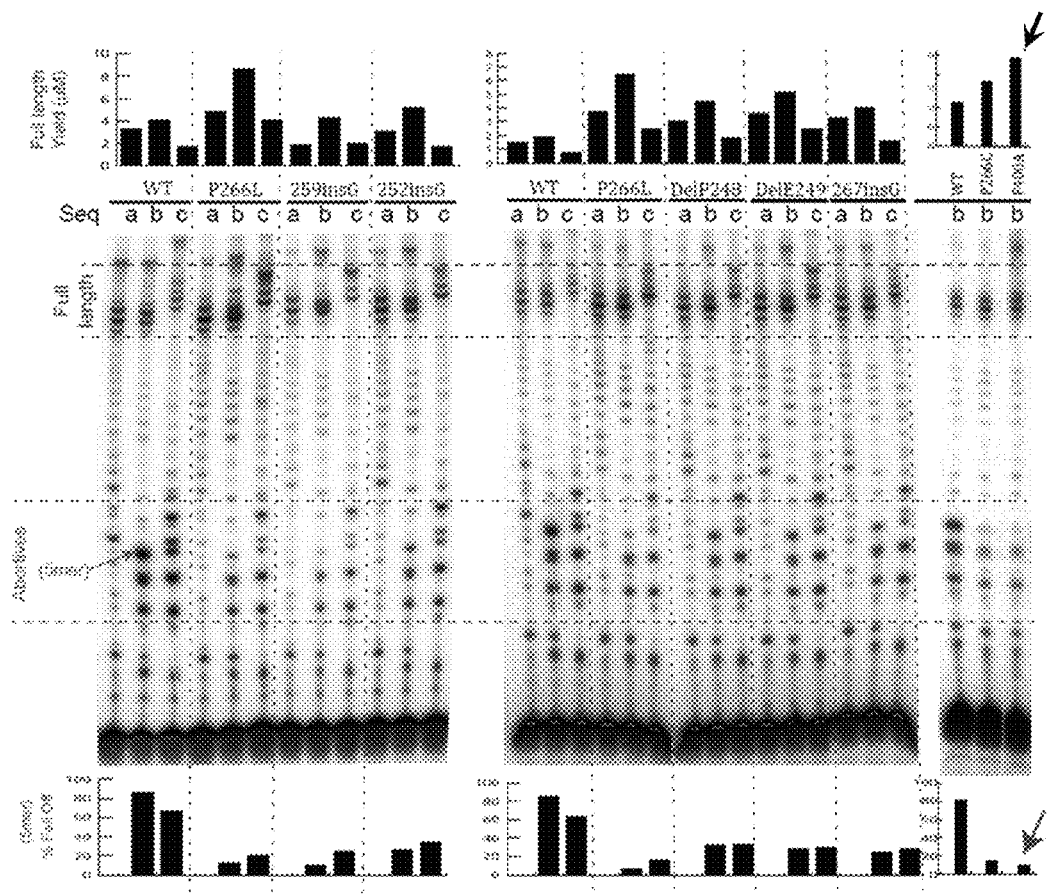
FIG. 9 depicts a series of T7 RNA polymerase mutants with significantly reduced abortive profiles.

Mutant Forms of T7 RNA Polymerase for RNA Synthesis Dramatically Reduced Levels of Undesired (Short, Abortive) RNAs in Transcription Certain RNA polymerase yield substantial amounts of short, abortive products that complicate both the yield and the purity of the desired transcript. Mutants RNA polymerases were developed to obviate this problem. As shown in FIG. 9 (note quantification of "% Fall Off" of abortive 5mer RNA), abortive impurities are dramatically reduced in the mutants. FIG. 9 depicts the results of transcription on three different DNA sequences (a, b, c), with (a) being a sequence that natively yields relatively few abortives, while (b) and (c) are sequences that produce primarily abortive products with the wild type enzyme. For illustration, the lower bar chart quantifies the fraction of complexes that dissociate abortively at an RNA length of 5 on construct (b). When compared with the wild type T7 RNA polymerase, the new mutants show dramatically reduced 5mer (and other length) abortive fall off. This leads to a higher fraction of transcripts being the desired full length product, as quantified in the top bar chart. Based on mechanistic studies, mutants (FIG. 9; arrows at far right) showed yield and purity that exceeds previous standard (P266L). Since these mutations are mechanistically based, very similar mutations are indicated in the related T3 and SP6 expression systems.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

This invention is not limited in its application to the details of construction and the arrangement of components set forth in this description or illustrated in the drawings. The invention is capable of other embodiments and of being practiced or of being carried out in to various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. A modified T7-related RNA polymerase having an amino acid insertion of up to five amino acids within its C-linker motif compared with a corresponding native form of the modified T7-related RNA polymerase, wherein the amino acid sequence of the corresponding native form of the T7-related RNA polymerase is as set forth in SEQ ID NO: 1, and wherein the amino acid insertion is immediately before the amino acid at position 252 or 259 of the corresponding native form of the T7-related RNA polymerase.

2. The modified T7-related RNA polymerase of claim 1, wherein the insertion results in a reduced level of abortive product release compared with the corresponding native form of the T7-related RNA polymerase.

3. The modified T7-related RNA polymerase of claim 1, wherein the insertion results in a reduced energetic barrier to rotation of its N-terminal platform compared with the corresponding native form of the T7-related RNA polymerase.

4. The modified T7-related RNA polymerase of claim 1, wherein the insertion comprises a glycine, alanine, serine, threonine, cysteine, glutamine, asparagine, glutamate, aspartate, lysine, or arginine.

5. A modified T7-related RNA polymerase having the amino acid sequence of SEQ ID NO: 5 or 6.

6. A method for producing an RNA, the method comprising:
combining the modified T7-related RNA polymerase of claim 1 with a nucleic acid template that encodes the RNA and is operably linked with a promoter recognized by the modified T7-related RNA polymerase, under conditions suitable for RNA transcription, and maintaining the combination for a period of time sufficient to transcribe the RNA, thereby producing the RNA.

7. A method for producing a protein, the method comprising:
(i.) combining the modified T7-related RNA polymerase of claim 1 with a nucleic acid template that encodes an mRNA and is operably linked with a promoter recognized by the modified T7-related RNA polymerase, under conditions suitable for RNA transcription, and maintaining the combination for a period of time sufficient to transcribe the mRNA; and (ii.) subjecting the transcribed mRNA to a translation reaction, thereby producing the protein.

8. The method of claim 6, wherein compared with the corresponding native form of the T7-RNA polymerase, the modified T7-related RNA polymerase produces the RNA with less release of abortive RNA fragments.

9. A kit comprising a container housing the modified T7-related RNA polymerase of claim 1.

10. The kit of claim 9, further comprising container housing a reaction buffer.

11. The kit of claim 10, further comprising at least one container housing a reagent for preparing a labeled RNA probe or for performing an in vitro translation reaction.

12. The modified T7-related RNA polymerase of claim 1, wherein the amino acid insertion comprises glycine and/or alanine residues.

13. The modified T7-related RNA polymerase of claim 1 wherein the amino acid insertion is up to four amino acids.

14. The modified T7-related RNA polymerase of claim 1 wherein the amino acid insertion is up to three amino acids.

15. The modified T7-related RNA polymerase of claim 1 wherein the amino acid insertion is up to two amino acids.

16. The modified T7-related RNA polymerase of claim 1 wherein the amino acid insertion is one amino acid.

17. The modified T7-related RNA polymerase of claim 5 having the amino acid sequence of SEQ ID NO: 5.

18. A method for producing an RNA, the method comprising:
combining the modified T7-related RNA polymerase of claim 17 with a nucleic acid template that encodes the RNA and is operably linked with a promoter recognized by the modified T7-related RNA polymerase, under conditions suitable for RNA transcription, and maintaining the combination for a period of time sufficient to transcribe the RNA, thereby producing the RNA.

19. A method for producing a protein, the method comprising:
(i.) combining the modified T7-related RNA polymerase of claim 17 with a nucleic acid template that encodes an mRNA and is operably linked with a promoter recognized by the modified T7-related RNA polymerase, under conditions suitable for RNA transcription, and maintaining the combination for a period of time sufficient to transcribe the mRNA; and (ii.) subjecting the transcribed mRNA to a translation reaction, thereby producing the protein.

20. A kit comprising a container housing the modified T7-related RNA polymerase of claim 17.

21. The kit of claim 20, further comprising container housing a reaction buffer.

22. The kit of claim 20, further comprising at least one container housing a reagent for preparing a labeled RNA probe or for performing an in vitro translation reaction.

23. The modified T7-related RNA polymerase of claim 5 having the amino acid sequence of SEQ ID NO: 6.

24. A method for producing an RNA, the method comprising:
combining the modified T7-related RNA polymerase of claim 23 with a nucleic acid template that encodes the RNA and is operably linked with a promoter recognized by the modified T7-related RNA polymerase, under conditions suitable for RNA transcription, and maintaining the combination for a period of time sufficient to transcribe the RNA, thereby producing the RNA.

25. A method for producing a protein, the method comprising:
(i.) combining the modified T7-related RNA polymerase of claim 23 with a nucleic acid template that encodes an mRNA and is operably linked with a promoter recognized by the modified T7-related RNA polymerase, under conditions suitable for RNA transcription, and maintaining the combination for a period of time sufficient to transcribe the mRNA; and (ii.) subjecting the transcribed mRNA to a translation reaction, thereby producing the protein.

26. A kit comprising a container housing the modified T7-related RNA polymerase of claim 23.

27. The kit of claim 26, further comprising container housing a reaction buffer.

28. The kit of claim 27, further comprising at least one container housing a reagent for preparing a labeled RNA probe or for performing an in vitro translation reaction.

29. The modified T7-related RNA polymerase of claim 5 further comprising an artificial tag, label, or chelating moiety.

* * * * *

SEQUENCE LISTING

```
<160> NUMBER OF SEQ ID NOS: 22

<210> SEQ ID NO 1
<211> LENGTH: 883
<212> TYPE: PRT
<213> ORGANISM: Artificial Sequence
<220> FEATURE:
<223> OTHER INFORMATION: Synthetic Polypeptide

<400> SEQUENCE: 1

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30
```

```
Ala Arg Glu Gln Leu Ala Leu Glu His Glu Ser Tyr Glu Met Gly Glu
             35                  40                  45

Ala Arg Phe Arg Lys Met Phe Glu Arg Gln Leu Lys Ala Gly Glu Val
 50                      55                  60

Ala Asp Asn Ala Ala Lys Pro Leu Ile Thr Thr Leu Leu Pro Lys
 65                  70                  75                  80

Met Ile Ala Arg Ile Asn Asp Trp Phe Glu Val Lys Ala Lys Arg
                 85                  90                  95

Gly Lys Arg Pro Thr Ala Phe Gln Phe Leu Gln Glu Ile Lys Pro Glu
             100                 105                 110

Ala Val Ala Tyr Ile Thr Ile Lys Thr Thr Leu Ala Cys Leu Thr Ser
             115                 120                 125

Ala Asp Asn Thr Thr Val Gln Ala Val Ala Ser Ala Ile Gly Arg Ala
             130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                 165                 170                 175

Val Tyr Lys Lys Ala Phe Met Gln Val Val Glu Ala Asp Met Leu Ser
             180                 185                 190

Lys Gly Leu Leu Gly Gly Glu Ala Trp Ser Ser Trp His Lys Glu Asp
             195                 200                 205

Ser Ile His Val Gly Val Arg Cys Ile Glu Met Leu Ile Glu Ser Thr
             210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                 245                 250                 255

Arg Ala Gly Ala Leu Ala Gly Ile Ser Pro Met Phe Gln Pro Cys Val
             260                 265                 270

Val Pro Pro Lys Pro Trp Thr Gly Ile Thr Gly Gly Gly Tyr Trp Ala
             275                 280                 285

Asn Gly Arg Arg Pro Leu Ala Leu Val Arg Thr His Ser Lys Lys Ala
             290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                 325                 330                 335

Val Ala Asn Val Ile Thr Lys Trp Lys His Cys Pro Val Glu Asp Ile
             340                 345                 350

Pro Ala Ile Glu Arg Glu Glu Leu Pro Met Lys Pro Glu Asp Ile Asp
             355                 360                 365

Met Asn Pro Glu Ala Leu Thr Ala Trp Lys Arg Ala Ala Ala Val
             370                 375                 380

Tyr Arg Lys Asp Arg Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                 405                 410                 415

Pro Tyr Asn Met Asp Trp Arg Gly Arg Val Tyr Ala Val Ser Met Phe
             420                 425                 430

Asn Pro Gln Gly Asn Asp Met Thr Lys Gly Leu Leu Thr Leu Ala Lys
             435                 440                 445
```

-continued

```
Gly Lys Pro Ile Gly Lys Glu Gly Tyr Tyr Trp Leu Lys Ile His Gly
450                 455                 460
Ala Asn Cys Ala Gly Val Asp Lys Val Pro Phe Pro Glu Arg Ile Lys
465                 470                 475                 480
Phe Ile Glu Glu Asn His Glu Asn Ile Met Ala Cys Ala Lys Ser Pro
                485                 490                 495
Leu Glu Asn Thr Trp Trp Ala Glu Gln Asp Ser Pro Phe Cys Phe Leu
            500                 505                 510
Ala Phe Cys Phe Glu Tyr Ala Gly Val Gln His His Gly Leu Ser Tyr
        515                 520                 525
Asn Cys Ser Leu Pro Leu Ala Phe Asp Gly Ser Cys Ser Gly Ile Gln
530                 535                 540
His Phe Ser Ala Met Leu Arg Asp Glu Val Gly Gly Arg Ala Val Asn
545                 550                 555                 560
Leu Leu Pro Ser Glu Thr Val Gln Asp Ile Tyr Gly Ile Val Ala Lys
                565                 570                 575
Lys Val Asn Glu Ile Leu Gln Ala Asp Ala Ile Asn Gly Thr Asp Asn
            580                 585                 590
Glu Val Val Thr Val Thr Asp Glu Asn Thr Gly Glu Ile Ser Glu Lys
        595                 600                 605
Val Lys Leu Gly Thr Lys Ala Leu Ala Gly Gln Trp Leu Ala His Gly
610                 615                 620
Val Thr Arg Ser Val Thr Lys Arg Ser Val Met Thr Leu Ala Tyr Gly
625                 630                 635                 640
Ser Lys Glu Phe Gly Phe Arg Gln Gln Val Leu Glu Asp Thr Ile Gln
                645                 650                 655
Pro Ala Ile Asp Ser Gly Lys Gly Pro Met Phe Thr Gln Pro Asn Gln
            660                 665                 670
Ala Ala Gly Tyr Met Ala Lys Leu Ile Trp Glu Ser Val Ser Val Thr
        675                 680                 685
Val Val Ala Ala Val Glu Ala Met Asn Trp Leu Lys Ser Ala Ala Lys
690                 695                 700
Leu Leu Ala Ala Glu Val Lys Asp Lys Thr Gly Glu Ile Leu Arg
705                 710                 715                 720
Lys Arg Cys Ala Val His Trp Val Thr Pro Asp Gly Phe Pro Val Trp
                725                 730                 735
Gln Glu Tyr Lys Lys Pro Ile Gln Thr Arg Leu Asn Leu Met Phe Leu
            740                 745                 750
Gly Gln Phe Arg Leu Gln Pro Thr Ile Asn Thr Asn Lys Asp Ser Glu
        755                 760                 765
Ile Asp Ala His Lys Gln Glu Ser Gly Ile Ala Pro Asn Phe Val His
770                 775                 780
Ser Gln Asp Gly Ser His Leu Arg Lys Thr Val Val Trp Ala His Glu
785                 790                 795                 800
Lys Tyr Gly Ile Glu Ser Phe Ala Leu Ile His Asp Ser Phe Gly Thr
                805                 810                 815
Ile Pro Ala Asp Ala Ala Asn Leu Phe Lys Ala Val Arg Glu Thr Met
            820                 825                 830
Val Asp Thr Tyr Glu Ser Cys Asp Val Leu Ala Asp Phe Tyr Asp Gln
        835                 840                 845
Phe Ala Asp Gln Leu His Glu Ser Gln Leu Asp Lys Met Pro Ala Leu
850                 855                 860
```

-continued

Pro Ala Lys Gly Asn Leu Asn Leu Arg Asp Ile Leu Glu Ser Asp Phe
865                 870                 875                 880

Ala Phe Ala

<210> SEQ ID NO 2
<211> LENGTH: 884
<212> TYPE: PRT
<213> ORGANISM: Artificial Sequence
<220> FEATURE:
<223> OTHER INFORMATION: Synthetic Polypeptide

<400> SEQUENCE: 2

Met Asn Ile Ile Glu Asn Ile Glu Lys Asn Asp Phe Ser Glu Ile Glu
1               5                   10                  15

Leu Ala Ala Ile Pro Phe Asn Thr Leu Ala Asp His Tyr Gly Ser Ala
                20                  25                  30

Leu Ala Lys Glu Gln Leu Ala Leu Glu His Glu Ser Tyr Glu Leu Gly
            35                  40                  45

Glu Arg Arg Phe Leu Lys Met Leu Glu Arg Gln Ala Lys Ala Gly Glu
        50                  55                  60

Ile Ala Asp Asn Ala Ala Ala Lys Pro Leu Leu Ala Thr Leu Leu Pro
65                  70                  75                  80

Lys Leu Thr Thr Arg Ile Val Glu Trp Leu Glu Glu Tyr Ala Ser Lys
                85                  90                  95

Lys Gly Arg Lys Pro Ser Ala Tyr Ala Pro Leu Gln Leu Leu Lys Pro
            100                 105                 110

Glu Ala Ser Ala Phe Ile Thr Leu Lys Val Ile Leu Ala Ser Leu Thr
        115                 120                 125

Ser Thr Asn Met Thr Thr Ile Gln Ala Ala Ala Gly Met Leu Gly Lys
130                 135                 140

Ala Ile Glu Asp Glu Ala Arg Phe Gly Arg Ile Arg Asp Leu Glu Ala
145                 150                 155                 160

Lys His Phe Lys Lys His Val Glu Glu Gln Leu Asn Lys Arg His Gly
                165                 170                 175

Gln Val Tyr Lys Lys Ala Phe Met Gln Val Val Glu Ala Asp Met Ile
            180                 185                 190

Gly Arg Gly Leu Leu Gly Gly Glu Ala Trp Ser Ser Trp Asp Lys Glu
        195                 200                 205

Thr Thr Met His Val Gly Ile Arg Leu Ile Glu Met Leu Ile Glu Ser
210                 215                 220

Thr Gly Leu Val Glu Leu Gln Arg His Asn Ala Gly Asn Ala Gly Ser
225                 230                 235                 240

Asp His Glu Ala Leu Gln Leu Ala Gln Glu Tyr Val Asp Val Leu Ala
                245                 250                 255

Lys Arg Ala Gly Ala Leu Ala Gly Ile Ser Pro Met Phe Gln Pro Cys
            260                 265                 270

Val Val Pro Pro Lys Pro Trp Val Ala Ile Thr Gly Gly Gly Tyr Trp
        275                 280                 285

Ala Asn Gly Arg Arg Pro Leu Ala Leu Val Arg Thr His Ser Lys Lys
290                 295                 300

Gly Leu Met Arg Tyr Glu Asp Val Tyr Met Pro Glu Val Tyr Lys Ala
305                 310                 315                 320

Val Asn Leu Ala Gln Asn Thr Ala Trp Lys Ile Asn Lys Lys Val Leu
                325                 330                 335

-continued

```
Ala Val Val Asn Glu Ile Val Asn Trp Lys Asn Cys Pro Val Ala Asp
            340                 345                 350

Ile Pro Ser Leu Glu Arg Gln Glu Leu Pro Pro Lys Pro Asp Asp Ile
            355                 360                 365

Asp Thr Asn Glu Ala Ala Leu Lys Glu Trp Lys Lys Ala Ala Ala Gly
        370                 375                 380

Ile Tyr Arg Leu Asp Lys Ala Arg Val Ser Arg Ile Ser Leu Glu
385                 390                 395                 400

Phe Met Leu Glu Gln Ala Asn Lys Phe Ala Ser Lys Lys Ala Ile Trp
                405                 410                 415

Phe Pro Tyr Asn Met Asp Trp Arg Gly Arg Val Tyr Ala Val Pro Met
            420                 425                 430

Phe Asn Pro Gln Gly Asn Asp Met Thr Lys Gly Leu Leu Thr Leu Ala
            435                 440                 445

Lys Gly Lys Pro Ile Gly Glu Glu Gly Phe Tyr Trp Leu Lys Ile His
        450                 455                 460

Gly Ala Asn Cys Ala Gly Val Asp Lys Val Pro Phe Pro Glu Arg Ile
465                 470                 475                 480

Ala Phe Ile Glu Lys His Val Asp Asp Ile Leu Ala Cys Ala Lys Asp
                485                 490                 495

Pro Ile Asn Asn Thr Trp Trp Ala Glu Gln Asp Ser Pro Phe Cys Phe
            500                 505                 510

Leu Ala Phe Cys Phe Glu Tyr Ala Gly Val Thr His His Gly Leu Ser
            515                 520                 525

Tyr Asn Cys Ser Leu Pro Leu Ala Phe Asp Gly Ser Cys Ser Gly Ile
            530                 535                 540

Gln His Phe Ser Ala Met Leu Arg Asp Glu Val Gly Gly Arg Ala Val
545                 550                 555                 560

Asn Leu Leu Pro Ser Glu Thr Val Gln Asp Ile Tyr Gly Ile Val Ala
            565                 570                 575

Gln Lys Val Asn Glu Ile Leu Lys Gln Asp Ala Ile Asn Gly Thr Pro
            580                 585                 590

Asn Glu Met Ile Thr Val Thr Asp Lys Asp Thr Gly Glu Ile Ser Glu
            595                 600                 605

Lys Leu Lys Leu Gly Thr Ser Thr Leu Ala Gln Gln Trp Leu Ala Tyr
        610                 615                 620

Gly Val Thr Arg Ser Val Thr Lys Arg Ser Val Met Thr Leu Ala Tyr
625                 630                 635                 640

Gly Ser Lys Glu Phe Gly Phe Arg Gln Gln Val Leu Asp Asp Thr Ile
                645                 650                 655

Gln Pro Ala Ile Asp Ser Gly Lys Gly Leu Met Phe Thr Gln Pro Asn
            660                 665                 670

Gln Ala Ala Gly Tyr Met Ala Lys Leu Ile Trp Asp Ala Val Ser Val
            675                 680                 685

Thr Val Val Ala Ala Val Glu Ala Met Asn Trp Leu Lys Ser Ala Ala
        690                 695                 700

Lys Leu Leu Ala Ala Glu Val Lys Asp Lys Thr Lys Glu Ile Leu
705                 710                 715                 720

Arg His Arg Cys Ala Val His Trp Thr Thr Pro Asp Gly Phe Pro Val
                725                 730                 735

Trp Gln Glu Tyr Arg Lys Pro Leu Gln Lys Arg Leu Asp Met Ile Phe
            740                 745                 750
```

```
Leu Gly Gln Phe Arg Leu Gln Pro Thr Ile Asn Thr Leu Lys Asp Ser
            755                 760                 765

Gly Ile Asp Ala His Lys Gln Glu Ser Gly Ile Ala Pro Asn Phe Val
        770                 775                 780

His Ser Gln Asp Gly Ser His Leu Arg Met Thr Val Val Tyr Ala His
785                 790                 795                 800

Glu Lys Tyr Gly Ile Glu Ser Phe Ala Leu Ile His Asp Ser Phe Gly
                805                 810                 815

Thr Ile Pro Ala Asp Ala Gly Lys Leu Phe Lys Ala Val Arg Glu Thr
                820                 825                 830

Met Val Ile Thr Tyr Glu Asn Asn Asp Val Leu Ala Asp Phe Tyr Ser
        835                 840                 845

Gln Phe Ala Asp Gln Leu His Glu Thr Gln Leu Asp Lys Met Pro Pro
850                 855                 860

Leu Pro Lys Lys Gly Asn Leu Asn Leu Gln Asp Ile Leu Lys Ser Asp
865                 870                 875                 880

Phe Ala Phe Ala

<210> SEQ ID NO 3
<211> LENGTH: 874
<212> TYPE: PRT
<213> ORGANISM: Artificial Sequence
<220> FEATURE:
<223> OTHER INFORMATION: Synthetic Polypeptide

<400> SEQUENCE: 3

Met Gln Asp Leu His Ala Ile Gln Leu Gln Leu Glu Glu Glu Met Phe
1               5                   10                  15

Asn Gly Gly Ile Arg Arg Phe Glu Ala Asp Gln Gln Arg Gln Ile Ala
                20                  25                  30

Ala Gly Ser Glu Ser Asp Thr Ala Trp Asn Arg Arg Leu Leu Ser Glu
            35                  40                  45

Leu Ile Ala Pro Met Ala Glu Gly Ile Gln Ala Tyr Lys Glu Glu Tyr
        50                  55                  60

Glu Gly Lys Lys Gly Arg Ala Pro Arg Ala Leu Ala Phe Leu Gln Cys
65                  70                  75                  80

Val Glu Asn Glu Val Ala Ala Tyr Ile Thr Met Lys Val Val Met Asp
                85                  90                  95

Met Leu Asn Thr Asp Ala Thr Leu Gln Ala Ile Ala Met Ser Val Ala
                100                 105                 110

Glu Arg Ile Glu Asp Gln Val Arg Phe Ser Lys Leu Glu Gly His Ala
            115                 120                 125

Ala Lys Tyr Phe Glu Lys Val Lys Lys Ser Leu Lys Ala Ser Arg Thr
        130                 135                 140

Lys Ser Tyr Arg His Ala His Asn Val Ala Val Val Ala Glu Lys Ser
145                 150                 155                 160

Val Ala Glu Lys Asp Ala Asp Phe Asp Arg Trp Glu Ala Trp Pro Lys
                165                 170                 175

Glu Thr Gln Leu Gln Ile Gly Thr Thr Leu Leu Glu Ile Leu Glu Gly
            180                 185                 190

Ser Val Phe Tyr Asn Gly Glu Pro Val Phe Met Arg Ala Met Arg Thr
        195                 200                 205

Tyr Gly Gly Lys Thr Ile Tyr Tyr Leu Gln Thr Ser Glu Ser Val Gly
    210                 215                 220
```

-continued

Gln Trp Ile Ser Ala Phe Lys Glu His Val Ala Gln Leu Ser Pro Ala
225                 230                 235                 240

Tyr Ala Pro Cys Val Ile Pro Pro Arg Pro Trp Arg Thr Pro Phe Asn
                245                 250                 255

Gly Gly Phe His Thr Glu Lys Val Ala Ser Arg Ile Arg Leu Val Lys
            260                 265                 270

Gly Asn Arg Glu His Val Arg Lys Leu Thr Gln Lys Gln Met Pro Lys
        275                 280                 285

Val Tyr Lys Ala Ile Asn Ala Leu Gln Asn Thr Gln Trp Gln Ile Asn
    290                 295                 300

Lys Asp Val Leu Ala Val Ile Glu Glu Val Ile Arg Leu Asp Leu Gly
305                 310                 315                 320

Tyr Gly Val Pro Ser Phe Lys Pro Leu Ile Asp Lys Glu Asn Lys Pro
                325                 330                 335

Ala Asn Pro Val Pro Val Glu Phe Gln His Leu Arg Gly Arg Glu Leu
            340                 345                 350

Lys Glu Met Leu Ser Pro Glu Gln Trp Gln Gln Phe Ile Asn Trp Lys
        355                 360                 365

Gly Glu Cys Ala Arg Leu Tyr Thr Ala Glu Thr Lys Arg Gly Ser Lys
    370                 375                 380

Ser Ala Val Val Arg Met Val Gly Gln Ala Arg Lys Tyr Ser Ala
385                 390                 395                 400

Phe Glu Ser Ile Tyr Phe Val Tyr Ala Met Asp Ser Arg Ser Arg Val
                405                 410                 415

Tyr Val Gln Ser Ser Thr Leu Ser Pro Gln Ser Asn Asp Leu Gly Lys
            420                 425                 430

Ala Leu Leu Arg Phe Thr Glu Gly Arg Pro Val Asn Gly Val Glu Ala
        435                 440                 445

Leu Lys Trp Phe Cys Ile Asn Gly Ala Asn Leu Trp Gly Trp Asp Lys
    450                 455                 460

Lys Thr Phe Asp Val Arg Val Ser Asn Val Leu Asp Glu Glu Phe Gln
465                 470                 475                 480

Asp Met Cys Arg Asp Ile Ala Ala Asp Pro Leu Thr Phe Thr Gln Trp
                485                 490                 495

Ala Lys Ala Asp Ala Pro Tyr Glu Phe Leu Ala Trp Cys Phe Glu Tyr
            500                 505                 510

Ala Gln Tyr Leu Asp Leu Val Asp Glu Gly Arg Ala Asp Glu Phe Arg
        515                 520                 525

Thr His Leu Pro Val His Gln Asp Gly Ser Cys Ser Gly Ile Gln His
    530                 535                 540

Tyr Ser Ala Met Leu Arg Asp Glu Val Gly Ala Lys Ala Val Asn Leu
545                 550                 555                 560

Lys Pro Ser Asp Ala Pro Gln Asp Ile Tyr Gly Ala Val Ala Gln Val
                565                 570                 575

Val Ile Lys Lys Asn Ala Leu Tyr Met Asp Ala Asp Asp Ala Thr Thr
            580                 585                 590

Phe Thr Ser Gly Ser Val Thr Leu Ser Gly Thr Glu Leu Arg Ala Met
        595                 600                 605

Ala Ser Ala Trp Asp Ser Ile Gly Ile Thr Arg Ser Leu Thr Lys Lys
    610                 615                 620

Pro Val Met Thr Leu Pro Tyr Gly Ser Thr Arg Leu Thr Cys Arg Glu
625                 630                 635                 640

```
Ser Val Ile Asp Tyr Ile Val Asp Leu Glu Glu Lys Glu Ala Gln Lys
                645                 650                 655
Ala Val Ala Glu Gly Arg Thr Ala Asn Lys Val His Pro Phe Glu Asp
            660                 665                 670
Asp Arg Gln Asp Tyr Leu Thr Pro Gly Ala Ala Tyr Asn Tyr Met Thr
        675                 680                 685
Ala Leu Ile Trp Pro Ser Ile Ser Glu Val Val Lys Ala Pro Ile Val
    690                 695                 700
Ala Met Lys Met Ile Arg Gln Leu Ala Arg Phe Ala Ala Lys Arg Asn
705                 710                 715                 720
Glu Gly Leu Met Tyr Thr Leu Pro Thr Gly Phe Ile Leu Glu Gln Lys
                725                 730                 735
Ile Met Ala Thr Glu Met Leu Arg Val Arg Thr Cys Leu Met Gly Asp
            740                 745                 750
Ile Lys Met Ser Leu Gln Val Glu Thr Asp Ile Val Asp Glu Ala Ala
        755                 760                 765
Met Met Gly Ala Ala Pro Asn Phe Val His Gly His Asp Ala Ser
    770                 775                 780
His Leu Ile Leu Thr Val Cys Glu Leu Val Asp Lys Gly Val Thr Ser
785                 790                 795                 800
Ile Ala Val Ile His Asp Ser Phe Gly Thr His Ala Asp Asn Thr Leu
                805                 810                 815
Thr Leu Arg Val Ala Leu Lys Gly Gln Met Val Ala Met Tyr Ile Asp
            820                 825                 830
Gly Asn Ala Leu Gln Lys Leu Leu Glu Glu His Glu Glu Arg Trp Met
        835                 840                 845
Val Asp Thr Gly Ile Glu Val Pro Glu Gln Gly Glu Phe Asp Leu Asn
    850                 855                 860
Glu Ile Met Asp Ser Glu Tyr Val Phe Ala
865                 870

<210> SEQ ID NO 4
<211> LENGTH: 906
<212> TYPE: PRT
<213> ORGANISM: Artificial Sequence
<220> FEATURE:
<223> OTHER INFORMATION: Synthetic Polypeptide

<400> SEQUENCE: 4

Met Asn Ala Leu Asn Ile Gly Arg Asn Asp Phe Ser Glu Ile Glu Leu
1               5                   10                  15
Ala Ala Ile Pro Tyr Asn Ile Leu Ser Glu His Tyr Gly Asp Gln Ala
            20                  25                  30
Ala Arg Glu Gln Leu Ala Leu Glu His Glu Ala Tyr Glu Leu Gly Arg
        35                  40                  45
Gln Arg Phe Leu Lys Met Leu Glu Arg Gln Val Lys Ala Gly Glu Phe
    50                  55                  60
Ala Asp Asn Ala Ala Lys Pro Leu Val Leu Thr Leu His Pro Gln
65                  70                  75                  80
Leu Thr Lys Arg Ile Asp Asp Trp Lys Glu Gln Ala Asn Ala Arg
                85                  90                  95
Gly Lys Lys Pro Arg Ala Tyr Tyr Pro Ile Lys Gly Val Ala Ser
            100                 105                 110
Glu Leu Ala Val Ser Met Gly Ala Glu Val Leu Lys Glu Lys Arg Gly
        115                 120                 125
```

```
Val Ser Ser Glu Ala Ile Ala Leu Leu Thr Ile Lys Val Val Leu Gly
130                 135                 140

Asn Ala His Arg Pro Leu Lys Gly His Asn Pro Ala Val Ser Ser Gln
145                 150                 155                 160

Leu Gly Lys Ala Leu Glu Asp Glu Ala Arg Phe Gly Arg Ile Arg Glu
                165                 170                 175

Gln Glu Ala Ala Tyr Phe Lys Lys Asn Val Ala Asp Gln Leu Asp Lys
                180                 185                 190

Arg Val Gly His Val Tyr Lys Lys Ala Phe Met Gln Val Val Glu Ala
            195                 200                 205

Asp Met Ile Ser Lys Gly Met Leu Gly Gly Asp Asn Trp Ala Ser Trp
210                 215                 220

Lys Thr Asp Glu Gln Met His Val Gly Thr Lys Leu Leu Glu Leu Leu
225                 230                 235                 240

Ile Glu Gly Thr Gly Leu Val Glu Met Thr Lys Asn Lys Met Ala Asp
                245                 250                 255

Gly Ser Asp Asp Val Thr Ser Met Gln Met Val Gln Leu Ala Pro Ala
            260                 265                 270

Phe Val Glu Leu Leu Ser Lys Arg Ala Gly Ala Leu Ala Gly Ile Ser
            275                 280                 285

Pro Met His Gln Pro Cys Val Pro Pro Lys Pro Trp Val Glu Thr
290                 295                 300

Val Gly Gly Gly Tyr Trp Ser Val Gly Arg Arg Pro Leu Ala Leu Val
305                 310                 315                 320

Arg Thr His Ser Lys Lys Ala Leu Arg Arg Tyr Ala Asp Val His Met
                325                 330                 335

Pro Glu Val Tyr Lys Ala Val Asn Leu Ala Gln Asn Thr Pro Trp Lys
                340                 345                 350

Val Asn Lys Lys Val Leu Ala Val Val Asn Glu Ile Val Asn Trp Lys
            355                 360                 365

His Cys Pro Val Gly Asp Val Pro Ala Ile Glu Arg Glu Leu Pro
370                 375                 380

Pro Arg Pro Asp Asp Ile Asp Thr Asn Glu Val Ala Arg Lys Ala Trp
385                 390                 395                 400

Arg Lys Glu Ala Ala Ala Val Tyr Arg Lys Asp Lys Ala Arg Gln Ser
                405                 410                 415

Arg Arg Cys Arg Cys Glu Phe Met Val Ala Gln Ala Asn Lys Phe Ala
            420                 425                 430

Asn His Lys Ala Ile Trp Phe Pro Tyr Asn Met Asp Trp Arg Gly Arg
            435                 440                 445

Val Tyr Ala Val Ser Met Phe Asn Pro Gln Gly Asn Asp Met Thr Lys
            450                 455                 460

Gly Ser Leu Thr Leu Ala Lys Gly Lys Pro Ile Gly Leu Asp Gly Phe
465                 470                 475                 480

Tyr Trp Leu Lys Ile His Gly Ala Asn Cys Ala Gly Val Asp Lys Val
                485                 490                 495

Pro Phe Pro Glu Arg Ile Lys Phe Ile Glu Glu Asn Glu Gly Asn Ile
                500                 505                 510

Leu Ala Ser Ala Ala Asp Pro Leu Asn Asn Thr Trp Trp Thr Gln Gln
            515                 520                 525

Asp Ser Pro Phe Cys Phe Leu Ala Phe Cys Phe Glu Tyr Ala Gly Val
530                 535                 540
```

```
Lys His His Gly Leu Asn Tyr Asn Cys Ser Leu Pro Leu Ala Phe Asp
545                 550                 555                 560

Gly Ser Cys Ser Gly Ile Gln His Phe Ser Ala Met Leu Arg Asp Ser
            565                 570                 575

Ile Gly Gly Arg Ala Val Asn Leu Leu Pro Ser Asp Thr Val Gln Asp
        580                 585                 590

Ile Tyr Lys Ile Val Ala Asp Lys Val Asn Glu Val Leu His Gln His
    595                 600                 605

Ala Val Asn Gly Ser Gln Thr Val Val Glu Gln Ile Ala Asp Lys Glu
610                 615                 620

Thr Gly Glu Phe His Glu Lys Val Thr Leu Gly Glu Ser Val Leu Ala
625                 630                 635                 640

Ala Gln Trp Leu Gln Tyr Gly Val Thr Arg Lys Val Thr Lys Arg Ser
                645                 650                 655

Val Met Thr Leu Ala Tyr Gly Ser Lys Glu Ser Leu Val Arg Gln Gln
            660                 665                 670

Val Leu Glu Asp Thr Ile Gln Pro Ala Ile Asp Asn Gly Glu Gly Leu
        675                 680                 685

Met Phe Thr His Pro Asn Gln Ala Ala Gly Tyr Met Ala Lys Leu Ile
    690                 695                 700

Trp Asp Ala Val Thr Val Thr Val Val Ala Ala Val Glu Ala Met Asn
705                 710                 715                 720

Trp Leu Lys Ser Ala Ala Lys Leu Leu Ala Glu Val Lys Asp Lys
                725                 730                 735

Lys Thr Lys Glu Val Leu Arg Lys Arg Cys Ala Ile His Trp Val Thr
            740                 745                 750

Pro Asp Gly Phe Pro Val Trp Gln Glu Tyr Arg Lys Gln Asn Gln Ala
        755                 760                 765

Arg Leu Lys Leu Val Phe Leu Gly Gln Ala Asn Val Lys Met Thr Tyr
    770                 775                 780

Asn Thr Gly Lys Asp Ser Glu Ile Asp Ala His Lys Gln Glu Ser Gly
785                 790                 795                 800

Ile Ala Pro Asn Phe Val His Ser Gln Asp Gly Ser His Leu Arg Met
                805                 810                 815

Thr Val Val His Ala Asn Glu Val Tyr Gly Ile Asp Ser Phe Ala Leu
            820                 825                 830

Ile His Asp Ser Ser Gly Thr Ile Pro Ala Asp Ala Gly Asn Leu Phe
        835                 840                 845

Lys Ala Val Arg Glu Thr Met Val Lys Thr Tyr Glu Asp Asn Asp Val
    850                 855                 860

Ile Ala Asp Phe Tyr Asp Gln Phe Ala Asp Gln Leu His Glu Ser Gln
865                 870                 875                 880

Leu Asp Lys Met Pro Ala Val Pro Ala Lys Gly Asp Leu Asn Leu Arg
                885                 890                 895

Asp Ile Leu Glu Ser Asp Phe Ala Phe Ala
            900                 905
```

<210> SEQ ID NO 5
<211> LENGTH: 884
<212> TYPE: PRT
<213> ORGANISM: Artificial Sequence
<220> FEATURE:
<223> OTHER INFORMATION: Synthetic Polypeptide

<400> SEQUENCE: 5

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Gly Ala Leu Ala Gly Ile Ser Pro Met Phe Gln Pro Cys
            260                 265                 270

Val Val Pro Pro Lys Pro Trp Thr Gly Ile Thr Gly Gly Gly Tyr Trp
        275                 280                 285

Ala Asn Gly Arg Arg Pro Leu Ala Leu Val Arg Thr His Ser Lys Lys
    290                 295                 300

Ala Leu Met Arg Tyr Glu Asp Val Tyr Met Pro Glu Val Tyr Lys Ala
305                 310                 315                 320

Ile Asn Ile Ala Gln Asn Thr Ala Trp Lys Ile Asn Lys Lys Val Leu
                325                 330                 335

Ala Val Ala Asn Val Ile Thr Lys Trp Lys His Cys Pro Val Glu Asp
            340                 345                 350

Ile Pro Ala Ile Glu Arg Glu Leu Pro Met Lys Pro Glu Asp Ile
        355                 360                 365

Asp Met Asn Pro Glu Ala Leu Thr Ala Trp Lys Arg Ala Ala Ala
    370                 375                 380

Val Tyr Arg Lys Asp Arg Ala Arg Lys Ser Arg Ile Ser Leu Glu
385                 390                 395                 400

Phe Met Leu Glu Gln Ala Asn Lys Phe Ala Asn His Lys Ala Ile Trp
                405                 410                 415
```

```
Phe Pro Tyr Asn Met Asp Trp Arg Gly Arg Val Tyr Ala Val Ser Met
                420                 425                 430
Phe Asn Pro Gln Gly Asn Asp Met Thr Lys Gly Leu Leu Thr Leu Ala
            435                 440                 445
Lys Gly Lys Pro Ile Gly Lys Glu Gly Tyr Tyr Trp Leu Lys Ile His
450                 455                 460
Gly Ala Asn Cys Ala Gly Val Asp Lys Val Pro Phe Pro Glu Arg Ile
465                 470                 475                 480
Lys Phe Ile Glu Glu Asn His Glu Asn Ile Met Ala Cys Ala Lys Ser
                485                 490                 495
Pro Leu Glu Asn Thr Trp Trp Ala Glu Gln Asp Ser Pro Phe Cys Phe
            500                 505                 510
Leu Ala Phe Cys Phe Glu Tyr Ala Gly Val Gln His His Gly Leu Ser
        515                 520                 525
Tyr Asn Cys Ser Leu Pro Leu Ala Phe Asp Gly Ser Cys Ser Gly Ile
        530                 535                 540
Gln His Phe Ser Ala Met Leu Arg Asp Glu Val Gly Gly Arg Ala Val
545                 550                 555                 560
Asn Leu Leu Pro Ser Glu Thr Val Gln Asp Ile Tyr Gly Ile Val Ala
                565                 570                 575
Lys Lys Val Asn Glu Ile Leu Gln Ala Asp Ala Ile Asn Gly Thr Asp
            580                 585                 590
Asn Glu Val Val Thr Val Thr Asp Glu Asn Thr Gly Glu Ile Ser Glu
        595                 600                 605
Lys Val Lys Leu Gly Thr Lys Ala Leu Ala Gly Gln Trp Leu Ala His
610                 615                 620
Gly Val Thr Arg Ser Val Thr Lys Arg Ser Val Met Thr Leu Ala Tyr
625                 630                 635                 640
Gly Ser Lys Glu Phe Gly Phe Arg Gln Gln Val Leu Glu Asp Thr Ile
                645                 650                 655
Gln Pro Ala Ile Asp Ser Gly Lys Gly Pro Met Phe Thr Gln Pro Asn
            660                 665                 670
Gln Ala Ala Gly Tyr Met Ala Lys Leu Ile Trp Glu Ser Val Ser Val
        675                 680                 685
Thr Val Val Ala Ala Val Glu Ala Met Asn Trp Leu Lys Ser Ala Ala
        690                 695                 700
Lys Leu Leu Ala Ala Glu Val Lys Asp Lys Thr Gly Glu Ile Leu
705                 710                 715                 720
Arg Lys Arg Cys Ala Val His Trp Val Thr Pro Asp Gly Phe Pro Val
                725                 730                 735
Trp Gln Glu Tyr Lys Lys Pro Ile Gln Thr Arg Leu Asn Leu Met Phe
            740                 745                 750
Leu Gly Gln Phe Arg Leu Gln Pro Thr Ile Asn Thr Asn Lys Asp Ser
        755                 760                 765
Glu Ile Asp Ala His Lys Gln Glu Ser Gly Ile Ala Pro Asn Phe Val
        770                 775                 780
His Ser Gln Asp Gly Ser His Leu Arg Lys Thr Val Val Trp Ala His
785                 790                 795                 800
Glu Lys Tyr Gly Ile Glu Ser Phe Ala Leu Ile His Asp Ser Phe Gly
                805                 810                 815
Thr Ile Pro Ala Asp Ala Ala Asn Leu Phe Lys Ala Val Arg Glu Thr
            820                 825                 830
```

```
Met Val Asp Thr Tyr Glu Ser Cys Asp Val Leu Ala Asp Phe Tyr Asp
            835                 840                 845

Gln Phe Ala Asp Gln Leu His Glu Ser Gln Leu Asp Lys Met Pro Ala
850                 855                 860

Leu Pro Ala Lys Gly Asn Leu Asn Leu Arg Asp Ile Leu Glu Ser Asp
865                 870                 875                 880

Phe Ala Phe Ala

<210> SEQ ID NO 6
<211> LENGTH: 884
<212> TYPE: PRT
<213> ORGANISM: Artificial Sequence
<220> FEATURE:
<223> OTHER INFORMATION: Synthetic Polypeptide

<400> SEQUENCE: 6

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Gly Glu Ala Ile Ala
                245                 250                 255

Thr Arg Ala Gly Ala Leu Ala Gly Ile Ser Pro Met Phe Gln Pro Cys
            260                 265                 270

Val Val Pro Pro Lys Pro Trp Thr Gly Ile Thr Gly Gly Gly Tyr Trp
        275                 280                 285

Ala Asn Gly Arg Arg Pro Leu Ala Leu Val Arg Thr His Ser Lys Lys
    290                 295                 300
```

```
Ala Leu Met Arg Tyr Glu Asp Val Tyr Met Pro Glu Val Tyr Lys Ala
305                 310                 315                 320

Ile Asn Ile Ala Gln Asn Thr Ala Trp Lys Ile Asn Lys Lys Val Leu
            325                 330                 335

Ala Val Ala Asn Val Ile Thr Lys Trp Lys His Cys Pro Val Glu Asp
        340                 345                 350

Ile Pro Ala Ile Glu Arg Glu Glu Leu Pro Met Lys Pro Glu Asp Ile
    355                 360                 365

Asp Met Asn Pro Glu Ala Leu Thr Ala Trp Lys Arg Ala Ala Ala Ala
370                 375                 380

Val Tyr Arg Lys Asp Arg Ala Arg Lys Ser Arg Arg Ile Ser Leu Glu
385                 390                 395                 400

Phe Met Leu Glu Gln Ala Asn Lys Phe Ala Asn His Lys Ala Ile Trp
            405                 410                 415

Phe Pro Tyr Asn Met Asp Trp Arg Gly Arg Val Tyr Ala Val Ser Met
        420                 425                 430

Phe Asn Pro Gln Gly Asn Asp Met Thr Lys Gly Leu Leu Thr Leu Ala
    435                 440                 445

Lys Gly Lys Pro Ile Gly Lys Glu Gly Tyr Tyr Trp Leu Lys Ile His
450                 455                 460

Gly Ala Asn Cys Ala Gly Val Asp Lys Val Pro Phe Pro Glu Arg Ile
465                 470                 475                 480

Lys Phe Ile Glu Glu Asn His Glu Asn Ile Met Ala Cys Ala Lys Ser
            485                 490                 495

Pro Leu Glu Asn Thr Trp Trp Ala Glu Gln Asp Ser Pro Phe Cys Phe
        500                 505                 510

Leu Ala Phe Cys Phe Glu Tyr Ala Gly Val Gln His His Gly Leu Ser
    515                 520                 525

Tyr Asn Cys Ser Leu Pro Leu Ala Phe Asp Gly Ser Cys Ser Gly Ile
530                 535                 540

Gln His Phe Ser Ala Met Leu Arg Asp Glu Val Gly Gly Arg Ala Val
545                 550                 555                 560

Asn Leu Leu Pro Ser Glu Thr Val Gln Asp Ile Tyr Gly Ile Val Ala
            565                 570                 575

Lys Lys Val Asn Glu Ile Leu Gln Ala Asp Ala Ile Asn Gly Thr Asp
        580                 585                 590

Asn Glu Val Val Thr Val Thr Asp Glu Asn Thr Gly Glu Ile Ser Glu
    595                 600                 605

Lys Val Lys Leu Gly Thr Lys Ala Leu Ala Gly Gln Trp Leu Ala His
610                 615                 620

Gly Val Thr Arg Ser Val Thr Lys Arg Ser Val Met Thr Leu Ala Tyr
625                 630                 635                 640

Gly Ser Lys Glu Phe Gly Phe Arg Gln Gln Val Leu Glu Asp Thr Ile
            645                 650                 655

Gln Pro Ala Ile Asp Ser Gly Lys Gly Pro Met Phe Thr Gln Pro Asn
        660                 665                 670

Gln Ala Ala Gly Tyr Met Ala Lys Leu Ile Trp Glu Ser Val Ser Val
    675                 680                 685

Thr Val Val Ala Ala Val Glu Ala Met Asn Trp Leu Lys Ser Ala Ala
690                 695                 700

Lys Leu Leu Ala Ala Glu Val Lys Asp Lys Lys Thr Gly Glu Ile Leu
705                 710                 715                 720
```

```
Arg Lys Arg Cys Ala Val His Trp Val Thr Pro Asp Gly Phe Pro Val
            725                 730                 735

Trp Gln Glu Tyr Lys Lys Pro Ile Gln Thr Arg Leu Asn Leu Met Phe
            740                 745                 750

Leu Gly Gln Phe Arg Leu Gln Pro Thr Ile Asn Thr Asn Lys Asp Ser
            755                 760                 765

Glu Ile Asp Ala His Lys Gln Glu Ser Gly Ile Ala Pro Asn Phe Val
            770                 775                 780

His Ser Gln Asp Gly Ser His Leu Arg Lys Thr Val Val Trp Ala His
785                 790                 795                 800

Glu Lys Tyr Gly Ile Glu Ser Phe Ala Leu Ile His Asp Ser Phe Gly
            805                 810                 815

Thr Ile Pro Ala Asp Ala Ala Asn Leu Phe Lys Ala Val Arg Glu Thr
            820                 825                 830

Met Val Asp Thr Tyr Glu Ser Cys Asp Val Leu Ala Asp Phe Tyr Asp
            835                 840                 845

Gln Phe Ala Asp Gln Leu His Gly Ser Gln Leu Asp Lys Met Pro Ala
            850                 855                 860

Leu Pro Ala Lys Gly Asn Leu Asn Leu Arg Asp Ile Leu Glu Ser Asp
865                 870                 875                 880

Phe Ala Phe Ala

<210> SEQ ID NO 7
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 7

Glu Thr Ile Glu Leu Ala Pro Glu Tyr Ala Glu Ala Ile Ala Thr Arg
1               5                   10                  15

Ala Gly Ala Leu Ala Gly Ile Ser Pro Met Phe Gln Pro Cys Val
            20                  25                  30

<210> SEQ ID NO 8
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 8

Glu Ala Leu Gln Leu Ala Gln Gly Tyr Val Asp Val Leu Ala Lys Arg
1               5                   10                  15

Ala Gly Ala Leu Ala Gly Ile Ser Pro Met Phe Gln Pro Cys Val
            20                  25                  30

<210> SEQ ID NO 9
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 9

Gln Met Val Gln Leu Ala Pro Ala Phe Val Glu Leu Leu Ser Lys Arg
1               5                   10                  15

Ala Gly Ala Leu Ala Gly Ile Ser Pro Met His Gln Pro Cys Val
            20                  25                  30
```

```
<210> SEQ ID NO 10
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 10

Glu Tyr Ile Gln Leu Thr Glu Gln Tyr Val Asp Leu Leu Ser Lys Arg
1               5                   10                  15

Ala Gly Ala Leu Ala Ala Ile Ala Pro Met Tyr Gln Pro Cys Val
            20                  25                  30

<210> SEQ ID NO 11
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 11

Glu Ala Leu His Leu Ala Pro Glu Tyr Val Glu Lys Leu Thr Asn Arg
1               5                   10                  15

Ala His Ala Leu Ala Gly Ile Ser Pro Met Tyr Gln Pro Met Ile
            20                  25                  30

<210> SEQ ID NO 12
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 12

Asn Val Leu Glu Leu Glu Pro Gln Trp Val Glu Met Leu Asn Gln Arg
1               5                   10                  15

Ala Phe Thr Leu Ala Gly Val Asn Thr Tyr His Gln Pro Cys Val
            20                  25                  30

<210> SEQ ID NO 13
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 13

Tyr Tyr Leu Gln Thr Ser Glu Ser Val Gly Gln Trp Ile Ser Ala Phe
1               5                   10                  15

Lys Glu His Val Ala Gln Leu Ser Pro Ala Tyr Ala Pro Cys Val
            20                  25                  30

<210> SEQ ID NO 14
<211> LENGTH: 31
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: A or T
<220> FEATURE:
<221> NAME/KEY: MISC_FEATURE
<222> LOCATION: (3)..(3)
<223> OTHER INFORMATION: I or L
```

```
<220> FEATURE:
<221> NAME/KEY: MISC_FEATURE
<222> LOCATION: (4)..(4)
<223> OTHER INFORMATION: E or Q
<220> FEATURE:
<221> NAME/KEY: MISC_FEATURE
<222> LOCATION: (7)..(7)
<223> OTHER INFORMATION: P or Q
<220> FEATURE:
<221> NAME/KEY: MISC_FEATURE
<222> LOCATION: (10)..(10)
<223> OTHER INFORMATION: A or V
<220> FEATURE:
<221> NAME/KEY: MISC_FEATURE
<222> LOCATION: (11)..(11)
<223> OTHER INFORMATION: E or D
<220> FEATURE:
<221> NAME/KEY: MISC_FEATURE
<222> LOCATION: (12)..(12)
<223> OTHER INFORMATION: A or V
<220> FEATURE:
<221> NAME/KEY: MISC_FEATURE
<222> LOCATION: (13)..(13)
<223> OTHER INFORMATION: I or L
<220> FEATURE:
<221> NAME/KEY: MISC_FEATURE
<222> LOCATION: (15)..(15)
<223> OTHER INFORMATION: T or K

<400> SEQUENCE: 14

Glu Xaa Xaa Xaa Leu Ala Xaa Glu Tyr Xaa Xaa Xaa Xaa Ala Xaa Arg
1               5                   10                  15

Ala Gly Ala Leu Ala Gly Ile Ser Pro Met Phe Gln Pro Cys Val
            20                  25                  30

<210> SEQ ID NO 15
<211> LENGTH: 31
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: E, Q, N or Y
<220> FEATURE:
<221> NAME/KEY: MISC_FEATURE
<222> LOCATION: (2)..(2)
<223> OTHER INFORMATION: T, A, M, Y, or V
<220> FEATURE:
<221> NAME/KEY: MISC_FEATURE
<222> LOCATION: (3)..(3)
<223> OTHER INFORMATION: I, L, or V
<220> FEATURE:
<221> NAME/KEY: MISC_FEATURE
<222> LOCATION: (4)..(4)
<223> OTHER INFORMATION: E, Q, or H
<220> FEATURE:
<221> NAME/KEY: MISC_FEATURE
<222> LOCATION: (5)..(5)
<223> OTHER INFORMATION: L or T
<220> FEATURE:
<221> NAME/KEY: MISC_FEATURE
<222> LOCATION: (6)..(6)
<223> OTHER INFORMATION: A, T, E, or S
<220> FEATURE:
<221> NAME/KEY: MISC_FEATURE
<222> LOCATION: (7)..(7)
<223> OTHER INFORMATION: P, Q, or E
<220> FEATURE:
<221> NAME/KEY: MISC_FEATURE
<222> LOCATION: (8)..(8)
<223> OTHER INFORMATION: A, E, Q, or S
```

```
<220> FEATURE:
<221> NAME/KEY: MISC_FEATURE
<222> LOCATION: (9)..(9)
<223> OTHER INFORMATION: Y, F, W, or V
<220> FEATURE:
<221> NAME/KEY: MISC_FEATURE
<222> LOCATION: (10)..(10)
<223> OTHER INFORMATION: A, V, or G
<220> FEATURE:
<221> NAME/KEY: MISC_FEATURE
<222> LOCATION: (11)..(11)
<223> OTHER INFORMATION: Q, E, or D
<220> FEATURE:
<221> NAME/KEY: MISC_FEATURE
<222> LOCATION: (12)..(12)
<223> OTHER INFORMATION: A, V, L, K, M, or W
<220> FEATURE:
<221> NAME/KEY: MISC_FEATURE
<222> LOCATION: (13)..(13)
<223> OTHER INFORMATION: I or L
<220> FEATURE:
<221> NAME/KEY: MISC_FEATURE
<222> LOCATION: (14)..(14)
<223> OTHER INFORMATION: A, S, T, or N
<220> FEATURE:
<221> NAME/KEY: MISC_FEATURE
<222> LOCATION: (15)..(15)
<223> OTHER INFORMATION: T, K, N, Q, or A
<220> FEATURE:
<221> NAME/KEY: MISC_FEATURE
<222> LOCATION: (16)..(16)
<223> OTHER INFORMATION: R or F
<220> FEATURE:
<221> NAME/KEY: MISC_FEATURE
<222> LOCATION: (17)..(17)
<223> OTHER INFORMATION: A or K
<220> FEATURE:
<221> NAME/KEY: MISC_FEATURE
<222> LOCATION: (18)..(18)
<223> OTHER INFORMATION: G, H, F, or E
<220> FEATURE:
<221> NAME/KEY: MISC_FEATURE
<222> LOCATION: (19)..(19)
<223> OTHER INFORMATION: A, T, or H
<220> FEATURE:
<221> NAME/KEY: MISC_FEATURE
<222> LOCATION: (20)..(20)
<223> OTHER INFORMATION: L or V
<220> FEATURE:
<221> NAME/KEY: MISC_FEATURE
<222> LOCATION: (21)..(21)
<223> OTHER INFORMATION: A
<220> FEATURE:
<221> NAME/KEY: MISC_FEATURE
<222> LOCATION: (22)..(22)
<223> OTHER INFORMATION: G, A, or Q
<220> FEATURE:
<221> NAME/KEY: MISC_FEATURE
<222> LOCATION: (23)..(23)
<223> OTHER INFORMATION: I, V, or L
<220> FEATURE:
<221> NAME/KEY: MISC_FEATURE
<222> LOCATION: (24)..(24)
<223> OTHER INFORMATION: S, A, or N
<220> FEATURE:
<221> NAME/KEY: MISC_FEATURE
<222> LOCATION: (25)..(25)
<223> OTHER INFORMATION: P or T
<220> FEATURE:
<221> NAME/KEY: MISC_FEATURE
<222> LOCATION: (26)..(26)
<223> OTHER INFORMATION: M, Y, A
<220> FEATURE:
<221> NAME/KEY: MISC_FEATURE
<222> LOCATION: (27)..(27)
<223> OTHER INFORMATION: F, H, Y
```

```
<220> FEATURE:
<221> NAME/KEY: MISC_FEATURE
<222> LOCATION: (28)..(28)
<223> OTHER INFORMATION: Q or A
<220> FEATURE:
<221> NAME/KEY: MISC_FEATURE
<222> LOCATION: (29)..(29)
<223> OTHER INFORMATION: P
<220> FEATURE:
<221> NAME/KEY: MISC_FEATURE
<222> LOCATION: (30)..(30)
<223> OTHER INFORMATION: C or M
<220> FEATURE:
<221> NAME/KEY: MISC_FEATURE
<222> LOCATION: (31)..(31)
<223> OTHER INFORMATION: V or I

<400> SEQUENCE: 15

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

<210> SEQ ID NO 16
<211> LENGTH: 100
<212> TYPE: PRT
<213> ORGANISM: Artificial Sequence
<220> FEATURE:
<223> OTHER INFORMATION: Synthetic Polypeptide

<400> SEQUENCE: 16

Leu Ile Glu Ser Thr Gly Met Val Ser Leu His Arg Gln Asn Ala Gly
1               5                   10                  15

Val Val Gly Gln Asp Ser Glu Thr Ile Glu Leu Ala Pro Glu Tyr Ala
                20                  25                  30

Glu Ala Ile Ala Thr Arg Ala Gly Ala Leu Ala Gly Ile Ser Pro Met
            35                  40                  45

Phe Gln Pro Cys Val Val Pro Pro Lys Pro Trp Thr Ala Val Tyr Arg
    50                  55                  60

Lys Asp Lys Ala Arg Lys Ser Arg Arg Ile Ser Leu Glu Phe Met Leu
65                  70                  75                  80

Glu Gln Ala Asn Lys Phe Ala Asn His Lys Ala Ile Trp Phe Pro Tyr
                85                  90                  95

Asn Met Asp Trp
            100

<210> SEQ ID NO 17
<211> LENGTH: 100
<212> TYPE: PRT
<213> ORGANISM: Artificial Sequence
<220> FEATURE:
<223> OTHER INFORMATION: Synthetic Polypeptide

<400> SEQUENCE: 17

Leu Ile Glu Ser Thr Gly Leu Val Glu Leu Gln Arg His Asn Ala Gly
1               5                   10                  15

Asn Ala Gly Ser Asp His Glu Ala Leu Gln Leu Ala Gln Glu Tyr Val
                20                  25                  30

Asp Val Leu Ala Lys Arg Ala Gly Ala Leu Ala Gly Ile Ser Pro Met
            35                  40                  45

Phe Gln Pro Cys Val Val Pro Pro Lys Pro Trp Val Ala Leu Lys Glu
    50                  55                  60
```

```
Trp Lys Lys Ala Ala Gly Ile Tyr Arg Leu Asp Lys Ala Arg Val
 65                  70                  75                  80

Ser Arg Arg Ile Ser Leu Glu Phe Met Leu Glu Gln Ala Asn Lys Phe
                 85                  90                  95

Ala Ser Lys Lys
            100
```

<210> SEQ ID NO 18
<211> LENGTH: 103
<212> TYPE: PRT
<213> ORGANISM: Artificial Sequence
<220> FEATURE:
<223> OTHER INFORMATION: Synthetic Polypeptide

<400> SEQUENCE: 18

```
Leu Ile Glu Gly Thr Gly Leu Val Glu Met Thr Lys Asn Lys Met Ala
 1               5                  10                  15

Asp Gly Ser Asp Asp Val Thr Ser Met Gln Met Val Gln Leu Ala Pro
                20                  25                  30

Ala Phe Val Glu Leu Leu Ser Lys Arg Ala Gly Ala Leu Ala Gly Ile
             35                  40                  45

Ser Pro Met His Gln Pro Cys Val Val Pro Pro Lys Pro Trp Val Ala
 50                  55                  60

Arg Lys Ala Trp Arg Lys Glu Ala Ala Ala Val Tyr Arg Lys Asp Lys
 65                  70                  75                  80

Ala Arg Gln Ser Arg Arg Leu Ser Met Glu Phe Met Val Ala Gln Ala
                 85                  90                  95

Asn Lys Phe Ala Asn His Lys
            100
```

<210> SEQ ID NO 19
<211> LENGTH: 100
<212> TYPE: PRT
<213> ORGANISM: Artificial Sequence
<220> FEATURE:
<223> OTHER INFORMATION: Synthetic Polypeptide

<400> SEQUENCE: 19

```
Leu Ile Gly Ser Thr Gly Leu Val Glu Leu His Arg Pro Phe Ala Gly
 1               5                  10                  15

Asn Val Glu Lys Asp Gly Glu Tyr Ile Gln Leu Thr Glu Gln Tyr Val
                20                  25                  30

Asp Leu Leu Ser Lys Arg Ala Gly Ala Leu Ala Ala Ile Ala Pro Met
             35                  40                  45

Tyr Gln Pro Cys Val Val Pro Pro Lys Pro Trp Thr Ala Leu Lys Ala
 50                  55                  60

Trp Lys Lys Ala Ala Ser Ala Ile Tyr Arg Lys Glu Lys Ala Arg Val
 65                  70                  75                  80

Ser Arg Arg Met Ser Met Glu Phe Met Leu Gly Gln Ala Asn Lys Phe
                 85                  90                  95

Ala Gln Phe Lys
            100
```

<210> SEQ ID NO 20
<211> LENGTH: 100
<212> TYPE: PRT
<213> ORGANISM: Artificial Sequence
<220> FEATURE:
<223> OTHER INFORMATION: Synthetic Polypeptide

<400> SEQUENCE: 20

Leu Ile Glu Ala Thr Gly Met Val Gln Leu Glu Arg Lys Phe Lys Gly
1               5                   10                  15

Ile Pro Asp Lys Asp His Glu Ala Leu His Leu Ala Pro Glu Tyr Val
            20                  25                  30

Glu Lys Leu Thr Asn Arg Ala His Ala Leu Ala Gly Ile Ser Pro Met
        35                  40                  45

Tyr Gln Pro Met Ile Val Lys Pro Lys Arg Trp Thr Ser Leu Lys Lys
    50                  55                  60

Trp Lys Lys Ala Ala Ala Ile Tyr Arg Lys Glu Lys Ala Arg Gln
65                  70                  75                  80

Ser Arg Arg Ile Ser Leu Glu Phe Ala Leu Ser Gln Ala Asn Lys Phe
                85                  90                  95

Ser Lys Tyr Asn
            100

<210> SEQ ID NO 21
<211> LENGTH: 100
<212> TYPE: PRT
<213> ORGANISM: Artificial Sequence
<220> FEATURE:
<223> OTHER INFORMATION: Synthetic Polypeptide

<400> SEQUENCE: 21

Leu Ile Glu Ser Ser Gly Leu Val Arg Ile Thr Arg Arg Ser Ala Gly
1               5                   10                  15

Asn Val Lys Glu Asp Cys Asn Val Leu Glu Leu Glu Pro Gln Trp Val
            20                  25                  30

Glu Met Leu Asn Gln Arg Ala Phe Thr Leu Ala Gly Val Asn Thr Tyr
        35                  40                  45

His Gln Pro Cys Val Val Pro Pro Arg Pro Trp Thr Ala Arg Asn Ala
    50                  55                  60

Trp Lys Lys Gln Ala Ser Gly Val Tyr Arg Ser Glu Ser Ser Arg Val
65                  70                  75                  80

Ser Arg Arg Met Ser Leu Glu Thr Thr Leu Glu Thr Ala Arg Lys Phe
                85                  90                  95

Ala Asp Phe Glu
            100

<210> SEQ ID NO 22
<211> LENGTH: 103
<212> TYPE: PRT
<213> ORGANISM: Artificial Sequence
<220> FEATURE:
<223> OTHER INFORMATION: Synthetic Polypeptide

<400> SEQUENCE: 22

Leu Glu Gly Ser Val Phe Tyr Asn Gly Glu Pro Val Phe Met Arg Ala
1               5                   10                  15

Met Arg Thr Tyr Gly Gly Lys Thr Ile Tyr Tyr Leu Gln Thr Ser Glu
            20                  25                  30

Ser Val Gly Gln Trp Ile Ser Ala Phe Lys Glu His Val Ala Gln Leu
        35                  40                  45

Ser Pro Ala Tyr Ala Pro Cys Val Ile Pro Arg Pro Trp Arg Lys
    50                  55                  60

Glu Met Leu Ser Pro Glu Gln Trp Gln Gln Phe Ile Asn Trp Lys Gly
65                  70                  75                  80

-continued

```
Glu Cys Ala Arg Leu Tyr Thr Ala Glu Thr Lys Arg Gly Ser Lys Ser
                85                  90                  95

Ala Ala Val Val Arg Met Val
            100
```